US008822498B2

(12) United States Patent
Jones et al.

(10) Patent No.: US 8,822,498 B2
(45) Date of Patent: Sep. 2, 2014

(54) SYNTHESIS OF DEUTERATED CATECHOLS AND BENZO[D][1,3]DIOXOLES AND DERIVATIVES THEREOF

(75) Inventors: Andrew D. Jones, Needham, MA (US); Robert E. Zelle, Stow, MA (US); I. Robert Silverman, Arlington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 980 days.

(21) Appl. No.: 12/283,621

(22) Filed: Sep. 12, 2008

(65) Prior Publication Data
US 2009/0143432 A1 Jun. 4, 2009

Related U.S. Application Data

(60) Provisional application No. 60/993,565, filed on Sep. 13, 2007.

(51) Int. Cl.
*A61K 31/445* (2006.01)
*C07D 211/22* (2006.01)

(52) U.S. Cl.
USPC .......................................... 514/321; 546/197

(58) Field of Classification Search
USPC .......................................... 514/321; 546/197
See application file for complete search history.

(56) References Cited

U.S. PATENT DOCUMENTS

| | | | |
|---|---|---|---|
| 4,007,196 A | 2/1977 | Christensen et al. | |
| 4,585,777 A | 4/1986 | Lassen et al. | |
| 5,167,948 A * | 12/1992 | Wenzel | 424/1.49 |
| 5,597,826 A | 1/1997 | Howard et al. | |
| 5,874,447 A | 2/1999 | Benneker et al. | |
| 6,221,335 B1 | 4/2001 | Foster | |
| 6,376,531 B1 | 4/2002 | Bell | |
| 6,436,938 B1 | 8/2002 | Howard, Jr. | |
| 6,440,710 B1 | 8/2002 | Keinan et al. | |
| 6,603,008 B1 | 8/2003 | Ando et al. | |
| 6,720,003 B2 | 4/2004 | Chen et al. | |
| 7,517,990 B2 | 4/2009 | Ito et al. | |
| 7,678,914 B2 | 3/2010 | Tung | |
| 2002/0013372 A1 | 1/2002 | Ekins | |
| 2002/0137938 A1 | 9/2002 | Lucas | |
| 2003/0187269 A1 | 10/2003 | Curzons et al. | |
| 2006/0135615 A1 | 6/2006 | Alken | |
| 2007/0082929 A1 | 4/2007 | Gant et al. | |
| 2007/0112031 A1 | 5/2007 | Gant et al. | |
| 2007/0191381 A1 | 8/2007 | Tung | |
| 2007/0197695 A1 | 8/2007 | Potyen et al. | |
| 2008/0033011 A1 | 2/2008 | Tung | |
| 2008/0045588 A1 | 2/2008 | Gant et al. | |
| 2008/0103122 A1 | 5/2008 | Veltri | |
| 2008/0287495 A1 | 11/2008 | Tung | |
| 2010/0222589 A1 | 9/2010 | Tung | |

FOREIGN PATENT DOCUMENTS

| | | |
|---|---|---|
| EP | 0 877 023 A1 | 11/1998 |
| IN | 392/MUM/2006 | 3/2006 |
| WO | WO95/26325 | 10/1995 |
| WO | WO 01/04113 A2 | 1/2001 |
| WO | WO 2005/108385 A1 | 11/2005 |
| WO | WO 2007/016361 A2 | 2/2007 |
| WO | WO 2007/016431 A2 | 2/2007 |
| WO | WO 2007/058998 A2 | 5/2007 |
| WO | WO 2007/118651 A1 | 10/2007 |
| WO | WO 2007/146124 A2 | 12/2007 |
| WO | WO 2008/016677 A2 | 2/2008 |
| WO | WO 2009/035652 A1 | 3/2009 |

OTHER PUBLICATIONS

Heydorn "Paroxetine: a review . . . " Exp. Opin. Invest. Drugs vo. 8(4) p. 417-441 (1999).*
Metcalf et al. "Mode of action " . . . J. Agr, Food Chem. v.14(6) p. 555-562 (1966).*
Segura et al. "Synthesis of . . . " Bioorg. Chem. v.31, p. 248-258 (2003).*
Banijamali, A.R. et al., "Specific Deuteration of Phenols and Aromatic Ethers Using Boron Trifluoride and Deuterium Oxide," *J. Labelled Compounds Radiopharmaceuticals* 24(12):1479-1482 (1987).
Cabiddu, M.G. et al., "A Re-Examination of the Methylenation Reaction," *Tetrahedron* 59:4383-4387 (2003).
Clark, J.H. et al., "Hydrogen Bonding in Organic Synthesis IV: A Simple, High-Yield Method for the Methylenation of Catechols," *Tetrahedron Letters* 38:3361-3364 (1976).
Drag, M. et al., "First Example of the Chemical, Oxidative Cleavage of the C—P Bond in Aminophosphonate Chemistry. The Oxidation of 1-amino-1-(3,4-dihydroxyphenyl)Methylphosphonic acid by $NaIO_4$," *Chem. Commun.*:1132-1133 (2004).
Faull, K.F. et al., "Selected Ion Monitoring Assay for Biogenic Amine Metabolites and Probenecid in Human Lumbar Cerebrospinal Fluid," *J. Chromatography* 163 :337-349 (1979).
Fisher, M.B. et al., "The Complexities Inherent in Attempts to Decrease Drug Clearance by Blocking Sites of CYP-Mediated Metabolism," *Curr. Opin. Drug Discov.*, 9(1): 101-109 (2006).
Fishlock, D. and Williams, R.M., "Synthetic Studies on Et-743. Asymmetric, Stereocontrolled Construction of the Tetrahydroisoquinoline Core via Radical Cyclization on a Glyoxalimine," *Organic Letters* 8(15): 3299-3301 (2006).
Friedrich, L.E. and Schuster, G.B., "Irradiation of α,β-Unsaturated Ketones. Search for Intermediate Oxabicyclobutanes," *J. Am. Chem. Soc.* 94:1193-1199 (1972).
Guay, D. et al., "Discovery of L-791,943: A Potent, Selective, Non Emetic and Orally Active Phosphodiesterase-4 Inhibitor," *Bioorganic & Medicinal Chemistry Letters* 12:1457-1461 (2002).
Iwasa, K. et al., "Biotransformations of Protoberberines in Cell Cultures in Dicentra Spectablis," *Phytochemistry*, Pergamon Press, GB, vol. 46, No. 8, pp. 1359-1363 (1997).
Jacks, T.E. et al., "Development of a Scalable Process for CI-1034, an Endothelin Antagonist," *Organic Process Research & Development* 8:201-212 (2004).

(Continued)

*Primary Examiner* — Celia Chang
(74) *Attorney, Agent, or Firm* — McCarter & English, LLP; Steven G. Davis; Emily Dertz

(57) ABSTRACT

The present invention provides a convenient and efficient process for the synthesis of $d_2$-benzo[d][1,3]dioxoles.

4 Claims, 6 Drawing Sheets

(56) References Cited

OTHER PUBLICATIONS

Kalir, A. et al., "The Synthesis of Deuterium Enriched *Erythro-α-*Methylnorepinephrine and Norepinephrine," *J. Labelled Compounds Radiopharmaceuticals* 13(1):41-58 (1977).
Karoum, F. et al., "Mass Fragmentographic Determination of Some Acidic and Alcoholic Metabolites of Biogenic Amines in the Rat Brain," *J. Neurochemistry* 25:653-658 (1975).
Kushner, D.J. et al., "Pharmacological Uses and Perspectives of Heavy Water and Deuterated Compounds," *Can. J. Physiol. Pharmacol.*, 77(2): 79-88 (1999).
Li, X-C, et al., "Absolute Configuration, Conformation, and Chiral Properties of Flavanone-(3→8")-flavone Biflavonoids from *Rheedia acuminata*," *Tetrahedron* 58:8709-8717 (2002).
Marcantoni, E. et al., "Synthesis of Advanced Intermediates for the Preparation of Aza-Analogues of Podophyllotoxin," *Tetrahedron Letters* 45:2133-2136 (2004).
Metcalf, R.L. et al., "Mode of Action of Carbamate Synergists," *J. Agr. Food Chem.* 14(6):555-562 (1966).
Nurberdyev, R. et al., "Synthesis of Alkyl and Formyloximethylsubstituted Diauxospirans," *Izvestiya Akademii Nauk Turkmenskoi SSR*, 6:103-105 (1990).
Shankland, N. et al., "Constrained Rietveld Refinement of [β-$^1$H1]decadeuteriodopamine deuteriobromide using Powder Neutron Diffraction Data," *J. Chem. Soc., Faraday Trans.* 92(22):4555-4559 (1996).
Vining, R.F. et al., "Deuterium Exchange Labelling of Biologically Important Phenols, Indoles and Steroids," *J. Labelled Compounds Radiopharmaceuticals* 18(11):1683-1692 (1981).
Zelle, R.E. and McClellan, W.J., "A Simple, High-Yielding Method for the Methylenation of Catechols," *Tetrahedron Letters* 32(22):2461-2464 (1991).
Zeng, E. et al., "Synthesis and Characterization of a New Discotic Columnar Side-Chain Liquid Crystalline Polymer Deuterated for NMR Analysis," *Polymer* 43:2169-2178 (2002).
Notification of Transmittal of the International Search Report and the Written Opinion of the International Searching Authority, or the Declaration, International Application No. PCT/US2008/010643; Date of mailing Jan. 22, 2009.
Bertelsen, K.M. at al, "Apparent Mechanism-Based Inhibition of Human CYP2D6 in vitro by Paroxetine: Comparison with Fluoxetine and Quinidine", Drug Metab. Dispos, 31(3):289-293 (2003).
FDA Center for Drug Evaluation and Drug Research, NDA No. 21-299, Clinical Pharmacology and Biopharmaceutics Reviews, 2003.
Foster et al, "Deuterium isotope effects in studies of drug metabolism," Trends in Pharm. Sci., vol. 5. 524-527, (1984).
Fukuto, J.M. et al. "Determination of the Mechanism of Demethylenation of (Methylenedioxy)phenyl Compounds by Cytochrome P450 Using Deuterium Isotope Effects", J. Med Chem. 34:2871-2876 (1991).

Kaye, C.M. et al. "A review of the metabolism and pharmacokinetics of paroxetine in man", Acta Psychiatr. Scant. 80 (supp. 350):60-75 (1989).
Leis et al, "Stable isotope dilution negative on chemical ionization gas chromatography-mass spectrometry for the quantitative analysis of paroxetine in human plasma," J. Mass Spectrom. vol. 36 (8), 923-928 (2001).
PCT International Preliminary Report on Patentability mailed on Mar. 16, 2010, in connection with International Application No. PCT/US2008/010643.
International Search Report of the International Searching Authority, mailed May 21, 2007, issued in connection with International Patent Appln. No. PCT/US2006/29599.
Written Opinion of the International Searching Authority mailed May 21, 2007, issued in connection with International Patent Appln. No. PCT/US2006/29599.
PCT International Preliminary Report on Patentability mailed on May 15, 2008, in connection with International Application No. PCT/US2006/29599.
Baille, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Tonn G. R., et al., "Simultaneous Analysis of Diphenhydramine and a Stable Isotope Analog ($^2$H$_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Wolen, R. L., "The Application of Stable Isotopes to Studies of Drug Bioavailability and Bioequivalence," *J. Clin. Pharmacol.*, 26: 419-424 (1986).

* cited by examiner (I) SYNTHESIS OF DEUTERATED CATECHOLS AND BENZO[D][1,3]DIOXOLES AND DERIVATIVES THEREOF

RELATED APPLICATION

This application claims the benefit of U.S. Provisional Application No. 60/993,565, filed on Sep. 13, 2007. The entire teachings of the above application is incorporated herein by reference.

BACKGROUND OF THE INVENTION

It has been reported that improvements in drug performance can be achieved by incorporating deuterium into specific sites of the active agent of certain approved pharmaceuticals. Examples include paroxetine (see WO 2007/016431 and US2007/0112031) and tadalafil (see US2007/0191381). The above-mentioned drugs all comprise benzo[d][1,3]dioxole groups. The methylenedioxy carbon of the benzo[d][1,3] dioxole group in paroxetine and tadalafil is one of the positions where deuterium incorporation is reported to provide for improved drug performance. The structures of benzo[d] [1,3]dioxole and $d_2$-benzo[d][1,3]dioxole (i.e., benzo[d][1,3]dioxole with two deuteriums at the methylenedioxy carbon) are shown below:

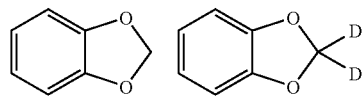

Benzo[d][1,3]dioxole    $d_2$-Benzo[d][1,3]dioxole

However, site-specific deuterium incorporation adds another level of complexity in developing suitable commercial syntheses. Specifically, reactions used to incorporate the deuterium should use reagents that are economical and that result in both a high chemical and isotopic yield. Total syntheses of paroxetine, tadalafil and the natural product berberine typically utilize benzo[d][1,3]dioxole derivatives as synthetic intermediates. Benzo[d][1,3]dioxole derivatives are typically made by reacting 1,2-catechols with dihalomethanes ($CH_2XY$, wherein X and Y are halides that are the same or different):

Using deuterated dihalomethanes ($CD_2XY$) to prepare $d_2$-benzo[d][1,3]dioxole results in low incorporation of deuterium into the benzo[d][1,3]dioxole product, i.e., typically no greater than about 94% deuterium incorporation at each labeled site:

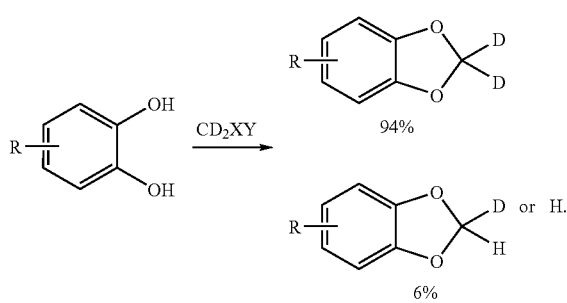

The low isotopic yield is less than desired for commercial syntheses of deuterated analogues of paroxetine, tadalafil and berberine comprising $d_2$-benzo[d][1,3]dioxole groups.

SUMMARY OF THE INVENTION

It has now been found that reacting deuterated dihalomethanes with catechols comprising deuterated phenolic groups increases the isotopic yield of the resulting $d_2$-benzo [d][1,3]dioxole to greater than 99.0% (see Examples 1-7). Based on this discovery, a novel two-step method for preparing $d_2$-benzo[d][1,3]dioxoles in high isotopic and chemical yield using inexpensive reagents is disclosed herein.

The first step of the process for preparing $d_2$-benzo[d][1,3]dioxole comprises reacting a catechol represented by Structural Formula (I) with a source of deuterium cation (also referred to herein as "D+") to form a deuterated catechol having an isotopic enrichment of deuterium of at least 75% and represented by Structural Formula (II):

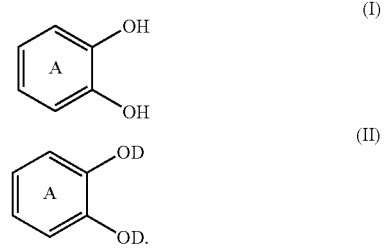

The second step of the process comprises reacting the deuterated catechol represented by Structural Formula (II) with a dihalodideuteromethane to form a $d_2$-benzo[d][1,3]dioxole represented by Structural Formula (III):

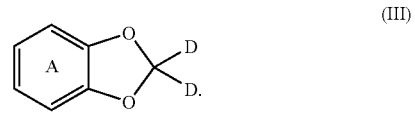

Ring A in the deuterated catechol and $d_2$-benzo[d][1,3]dioxole is substituted with one or more groups, provided that the substituent group(s) do not undergo significant reaction with the D+ source, the base when present, or the dihalodideuteromethane.

DETAILED DESCRIPTION OF THE INVENTION

Figure 1:
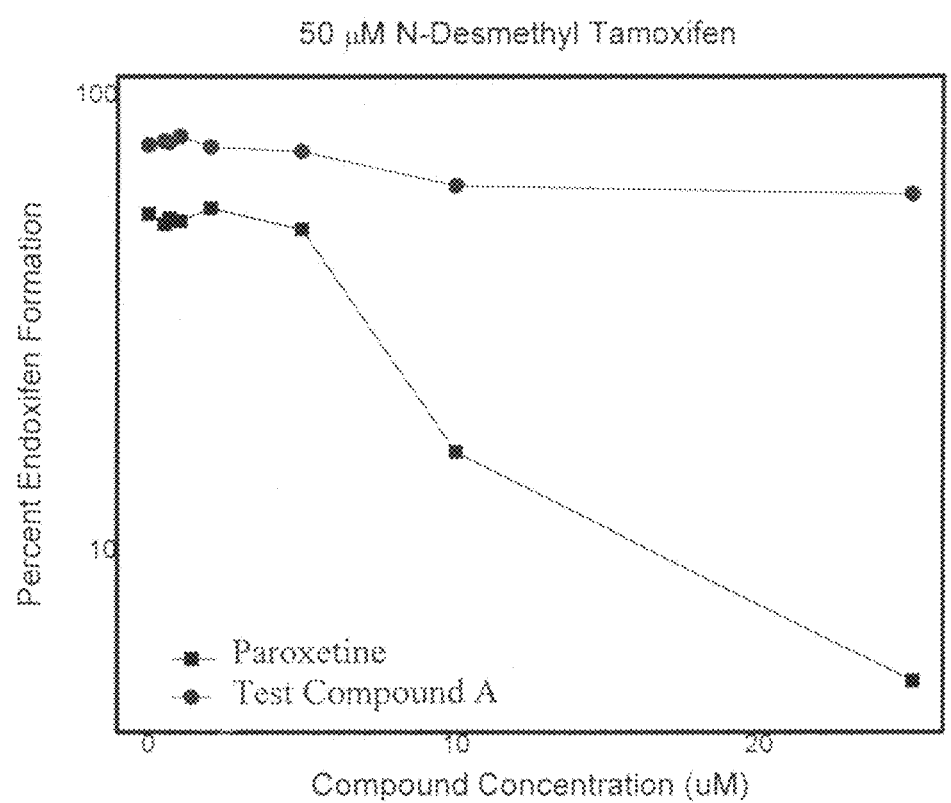
FIG. 1 depicts the drug-drug interaction potential between Test Compound A and tamoxifen.

A source of D+ is utilized when converting the catechol represented by Structural Formula (I) to the deuterated catechol represented by Structural Formula (II). This reaction is hereinafter referred to as the "Deuterium/Proton Exchange Reaction".

A source of deuterium cation is a compound having an exchangeable $D^+$, typically a compound having a $pK_a$ less than about 17 and which donates $D^+$ in place of a proton ($H^+$). Suitable examples include: i) solvents such as $D_2O$; ii) deuterated alcoholic solvents (ROD, where R is, for example, a $C_1$-$C_5$ straight or branched alkyl group) such as $CH_3OD$ and $CH_3CH_2OD$; and iii) acids such as DCl, $D_2SO_4$, $DNO_3$ and deuterated sulfonic acids (e.g., $CH_3SO_3D$). $D_2O$, $CH_3OD$ and DCl are most commonly used.

When the source of $D^+$ has a high $pK_a$ (e.g., $D_2O$ and $CH_3OD$), it is commonly used as the solvent. Other reagents can be added to increase the reaction rate. In one example, the other reagent is both a source of deuterium cation and a strong acid (e.g. DCl, $D_2SO_4$, $DNO_3$ and deuterated sulfonic acids such as $CH_3SO_3D$). Alternatively, the other reagent is a base that can deprotonate a phenolic group; to prevent isotopic dilution, potentially exchangeable protons in the base are preferably replaced with deuterium. Examples of suitable bases include NaH, MOD, $X(OD)_2$, MOR and $X(OR)_2$, wherein M is a monovalent cation such as $Li^+$, $Na^+$ or $K^+$; X is a divalent cation such as $Mg^{+2}$ and $Ca^{+2}$; and R is a $C_1$-$C_5$ straight or branched alkyl. Optionally, aprotic solvents that are miscible with $D_2O$ or $CH_3OD$ are added as co-solvents. Examples include tetrahydrofuran, N-methylpyrrolidinone, dimethylsulfoxide, acetonitrile and dioxane.

The Deuterium/Proton Exchange Reaction is commonly carried out at temperatures between room temperature and reflux for two to 48 hours (h); more commonly at room temperature for about 24 h.

The source of $D^+$ and the starting catechol are combined along with any other desired reagents either stepwise or in a single step to form a reaction mixture, thereby reacting the starting catechol and the $D^+$ source. Following completion of the reaction, the deuterated catechol product is isolated or separated from the $D^+$ source. The resulting composition comprises the deuterated catechol and is substantially free of the $D^+$ source, i.e., less than 10%, preferably less than 5%, more preferably less than 2% and even more preferably less than 1% by weight of the isolated composition is $D^+$ source. The deuterated catechol can be separated from the $D^+$ source by any suitable means, including by evaporation in vacuo when the $D^+$ source is a liquid or solvent. The resulting deuterated catechol in the composition can, if desired, be further purified by any suitable means, including crystallization or chromatography. The purity of the composition typically is at least 90%, 95%, 98% or 99% by weight deuterated catechol.

The reaction between the deuterated catechol and the deuterated dihalodeuteromethane is referred to herein as the "Alkylation Reaction". The Alkylation Reaction utilizes a deuterated catechol starting material represented by structural Formula (II) that has a deuterium isotope enrichment of at least 75%, preferably at least 80%, more preferably at least 85%, even more preferably at least 90% and even more preferably at least 95%. Deuterium enrichments corresponding to these levels can be obtained using the Deuterium/Proton Exchange Reaction (see Example 2). The percent deuterium isotope enrichment is defined as the actual number of moles of deuterium present at those positions designated as being labeled with deuterium divided by the theoretical maximum number of moles of deuterium that can be present at those positions. For example, in the benzo[d][1,3]dioxole represented by Structural Formula (III), theoretically, there are two moles of deuterium for every mole of benzo[d][1,3]dioxole. A deuterium enrichment of 85% means that there are 1.7 moles of deuterium for every mole of benzo[d][1,3]dioxole. Isotopic enrichment is routinely determined by $^1$H NMR analysis.

Dihalodeuteromethane is represented by $CD_2XY$, wherein X and Y are halides and can be the same or different. Examples include $CD_2Cl_2$, $CD_2Br_2$, $CD_2I_2$ or $BrCD_2Cl$. $CD_2Cl_2$ and $CD_2Br_2$ are more commonly used; and $CD_2Cl_2$ is most commonly used. The reaction is typically carried out in polar aprotic solvents such as N-methylpyrrolidinone, dimethylformamide, acetonitrile, hexamethylphosphoramide or N,N-dimethylpropyleneurea. In one embodiment, N-methylpyrrolidinone and dimethylformamide are used; in another embodiment dimethylformamide is used; and in another embodiment a mixture of N-methylpyrrolidinone and $D_2O$ is used. Between 5 and 20 volumes of solvent relative to catechol are commonly used; typically between 10 and 20 volumes are used.

Typically, the Alkylation Reaction is carried out in the presence of a base. Examples include carbonate bases (e.g., $K_2CO_3$ and $Cs_2CO_3$), alkoxide bases (e.g., $NaOCH_3$ and potassium tert-butoxide), hydride bases (e.g., NaH) and fluoride bases (e.g., KF and CsF). Between 2 and 4 equivalents of base relative to the catechol are typically used, more commonly between 2.0 and 2.2 equivalents are used.

The Alkylation Reaction is commonly carried out at a temperature between room temperature and 130° C. for 1 to 24 h. More commonly, the temperature is between 90 and 110° C. for between 1 and 4 h; and most commonly, the temperature is 110° C. for about 1.5 h.

The deuterium isotope enrichment in the deuterated benzo[d][1,3]dioxoles disclosed herein is typically greater than 99.0%, more commonly greater than 99.5% and even more commonly greater than 99.9%.

In a specific embodiment, the deuterated catechol starting material used and the deuterated benzo[d][1,3]dioxole formed in the Alkylation Reaction are represented by Structural Formula (IV) and Structural Formula (V), respectively. The deuterated catechol starting material has a deuterium isotope enrichment of at least 75%, preferably at least 80%, more preferably at least 85%, even more preferably at least 90% and even more preferably at least 95%:

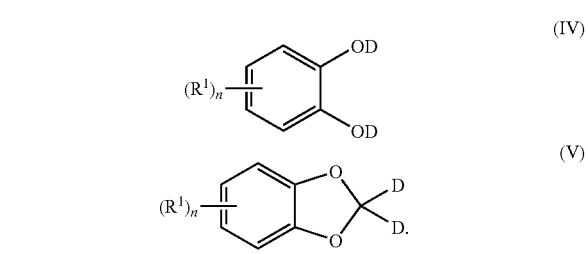

n is 1, 2 or 3.

Each R' is independently halo; —OR$^a$; OR'; —CHO; —COOR$^b$; —COOR'; C(O)R'; —CN; —OC(O)NH$_2$; —OC(O)NHR'; —OC(O)N(R')$_2$; —CR$^4$=C(R$^4$)$_2$; —C≡CR$^4$; or an aryl group optionally substituted with one or more groups represented by R$^5$.

Each R$^4$ is independently —H or a group represented by R';
Each R$^5$ is independently selected from halo; alkyl; —OR$^a$; alkoxy; haloalkoxy; —CHO; —COOR$^b$; —COOR"; C(O)R"; —NO$_2$; haloalkyl; —CN; NHR$^c$; —NR$^c$R"; —N(R")$_2$; —NHC(O)R"; —NHC(O)NH$_2$; —NHC(O)NHR"; —NHC(O)N(R")$_2$; —OC(O)NH$_2$; —OC(O)NHR";

—OC(O)N(R")$_2$; —NHC(O)H; —NHC(O)R"; —NHC(O)OR"; —S(O)R"; —S(O)$_2$R"; —SO$_2$NH$_2$; —SO$_2$NHR"; —SO$_2$N(R")$_2$; —NHSO$_2$NH$_2$; —NHSO$_2$NHR"; —NHSO$_2$N(R")$_2$; and —NHSO$_2$R".

R' is alkyl or aryl, each of which is optionally and independently substituted with one or more groups selected from halo; —OR$^a$; alkoxy; haloalkoxy; —CHO; —COOR$^b$; —COOR"; C(O)R"; —NO$_2$; alkyl; haloalkyl; —CN; —NHR$^c$; —NR$^c$R"; —N(R")$_2$; —NHC(O)R"; —NHC(O)NH$_2$; —NHC(O)NHR"; —NHC(O)N(R")$_2$; —OC(O)NH$_2$; —OC(O)NHR"; —OC(O)N(R")$_2$; —NHC(O)H; —NHC(O)R"; —NHC(O)OR"; —S(O)R"; —S(O)$_2$R"; —SO$_2$NH$_2$; —SO$_2$NHR"; —SO$_2$N(R")$_2$; —NHSO$_2$NH$_2$; —NHSO$_2$NHR"; —NHSO$_2$N(R")$_2$; and —NHSO$_2$R".

R" is alkyl.
R$^a$ is a phenol protecting group.
R$^b$ is a carboxylic acid protecting group.
R$^c$ is an amine protecting group.
Preferably for Structural Formulas (IV) and (V):
n is 1.
R' is halo; —OR$^a$; —OR'; —CHO; —COOR$^b$; —COOR'; C(O)R'; —CN; —CH=CHR$^4$; —C≡CH; —C≡CR$^4$; or a phenyl group optionally substituted with one or more groups represented by R$^5$.
Each R$^5$ is independently selected from halo; alkyl; —OR$^a$; alkoxy; haloalkoxy; —CHO; —COOR$^b$; —COOR"; C(O)R"; —NO$_2$; haloalkyl; and —CN.
R' is an alkyl; or a phenyl group optionally substituted with halo; —OR$^a$; alkoxy; haloalkoxy; —CHO; —COOR$^b$; —COOR"; C(O)R"; —NO$_2$; alkyl; haloalkyl; or —CN; and
the remainder of the variables are as described above.

In another embodiment, the deuterated catechol starting material used in the Alkylation Reaction is represented by Structural Formula (IVa) or (IVb) and the deuterated benzo[d][1,3]dioxole formed in the Alkylation Reaction is represented by Structural Formula (Va) or (Vb), respectively. The deuterated catechol starting material has a deuterium isotope enrichment of at least 75%, preferably at least 80%, more preferably at least 85%, even more preferably at least 90% and even more preferably at least 95%.

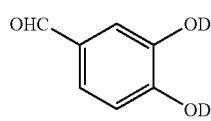
(IVa)

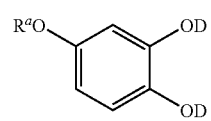
(IVb)

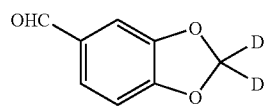
(Va)

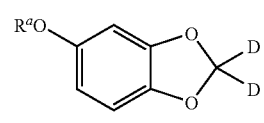
(Vb)

R$^a$ in Structural Formula (IVb) and (Vb) is a phenol protecting group.

In another specific embodiment, the catechol starting material and the deuterated catechol product in the Deuterium/Proton Exchange Reaction are represented by Structural Formula (VI) and Structural Formula (VII), respectively.

(VI)

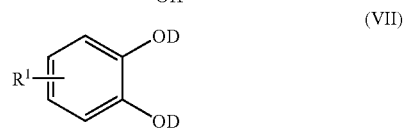
(VII)

R' is halo; —OR$^a$; alkoxy; —CHO; —COOR$^b$; —COOR'; C(O)R'; —CN; —CH=CHR$^4$; —C≡CH; —C≡CR$^4$; or a phenyl group optionally substituted with one or more groups represented by R$^5$;
R$^4$ is —H or a group represented by R';
each R$^5$ is independently selected from halo; alkyl; —OR$^a$; alkoxy; haloalkoxy; —CHO; —COOR$^b$; —COOR"; C(O)R"; —NO$_2$; haloalkyl; and —CN;
R' is alkyl; or a phenyl group optionally substituted with halo; —OR$^a$; alkoxy; haloalkoxy; —CHO; —COOR$^b$; —COOR"; C(O)R"; —NO$_2$; haloalkyl; or —CN;
R$^a$ is a phenol protecting group; and
R$^b$ is a carboxylic acid protecting group.

In another embodiment, catechol starting material and the deuterated catechol product in the Deuterium/Proton Exchange Reaction are represented by Structural Formula (VIII) and Structural Formula (IX), respectively:

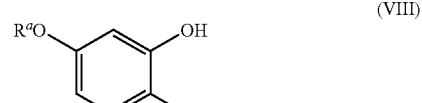
(VIII)

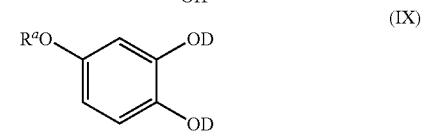
(IX)

wherein R$^a$ is a protecting group for a phenol.

In another embodiment, catechol starting material and the deuterated catechol product in the Deuterium/Proton Exchange Reaction are represented by Structural Formula (X) and Structural Formula (XI), respectively.

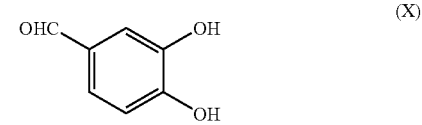
(X)

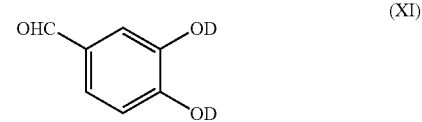
(XI)

The deuterated catechol represented by Structural Formula (VII), (IX) or (XI) is separated from the source of D$^+$, thereby resulting in a composition that comprises by weight less than 10%, preferably less than 5%, more preferably less than 2% and even more preferably less than 1% D⁺ source. The purity of the composition by weight is at least 90%, preferably 95%, more preferably 98% and even more preferably 99% deuterated catechol and the deuterated catechol has an isotopic enrichment of at least 75%, preferably at least 80%, more preferably at least 85%, even more preferably at least 90% and even more preferably at least 95%.

Another embodiment of the invention is a composition comprising a deuterated catechol represented by Structural Formula (VII), (IX) or (XI). This composition comprises by weight less than 10%, preferably less than 5%, more preferably less than 2% and even more preferably less than 1% D⁺ source; and/or has a purity of at least 90%, preferably 95%, more preferably 98% and even more preferably 99% by weight deuterated catechol. The deuterated catechol has an isotopic enrichment of at least 75%, preferably at least 80%, more preferably at least 85%, even more preferably at least 90% and even more preferably at least 95%.

Another embodiment of the invention is a deuterated benzo[d][1,3]dioxole represented by Structural Formula (XII):

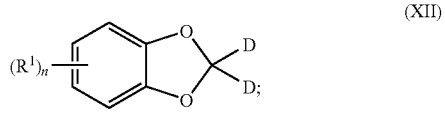

(XII)

The isotopic enrichment of the compound represented by Structural Formula (XII) is at least 99.0%; more commonly greater than 99.5% and even more commonly greater than 99.9%;

n is 1, 2 or 3;

each $R^1$ is independently fluoro; chloro; iodo; —$OR^a$; alkoxy; —CHO; —$COOR^b$; —COOR'; C(O)R'; —CN; —OC(O)N—$H_2$; —OC(O)NHR'; —OC(O)N(R')$_2$; —$CR^4$=C($R^4$)$_2$; —C≡C$R^4$; or an aryl group optionally substituted with one or more groups represented by $R^5$;

each $R^4$ is —H or a group represented by R';

each group represented by $R^5$ is independently halo; alkyl; —OR'; OR'; —CHO; —$COOR^b$; —COOR"; C(O)R"; —$NO_2$; haloalkyl; —CN; —$NHR^c$; —$NR^cR$"; —N(R")$_2$; —NHC(O)R"; —NHC(O)$NH_2$; —NHC(O)NHR"; —NHC(O)N(R")$_2$; —OC(O)$NH_2$; —OC(O)NHR"; —OC(O)N(R")$_2$; —NHC(O)H; —NHC(O)R"; —NHC(O)OR"; —S(O)R"; —S(O)$_2$R"; —$SO_2NH_2$; —$SO_2$NHR"; —$SO_2$N(R")$_2$; —$NHSO_2NH_2$; —$NHSO_2$NHR"; —$NHSO_2$N(R")$_2$; or —$NHSO_2$R";

R' is alkyl or aryl, each optionally and independently substituted with halo; —$OR^a$; alkoxy; haloalkoxy; —CHO; —$COOR^b$; —COOR"; C(O)R"; —$NO_2$; alkyl; haloalkyl; —CN; —$NHR^c$; —$NR^cR$"; —N(R")$_2$; —NHC(O)R"; —NHC(O)$NH_2$; —NHC(O)NHR"; —NHC(O)N(R")$_2$; —OC(O)$NH_2$; —OC(O)NHR"; —OC(O)N(R")$_2$; —NHC(O)H; —NHC(O)R"; —NHC(O)OR"; —S(O)R"; —S(O)$_2$R"; —$SO_2NH_2$; —$SO_2$NHR"; —$SO_2$N(R")$_2$; —$NHSO_2NH_2$; —$NHSO_2$NHR"; —$NHSO_2$N(R")$_2$; or —$NHSO_2$R";

R" is alkyl;

$R^a$ is —H or a phenol protecting group;

$R^b$ is —H or a carboxylic acid protecting group; and $R^c$ is —H or an amine protecting group.

In an alternative embodiment, the isotopic enrichment of the compound represented by Structural Formula (XII) is at least 96%, such as at least 97% and at least 98%, and all of the structural variables are as described above.

Another embodiment of the invention is a deuterated benzo[d][1,3]dioxole represented by Structural Formula (XIIa):

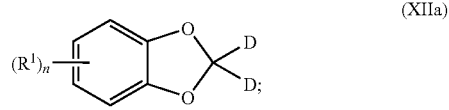

(XIIa)

The isotopic enrichment of the compound represented by Structural Formula (XIIa) is at least 99.0%; more commonly greater than 99.5% and even more commonly greater than 99.9%;

$R^1$ is fluoro; chloro; iodo; —$OR^a$; alkoxy; —CHO; —$COOR^b$; —COOR'; C(O)R'; —CH=CH$R^4$; —C≡CH; —C≡C$R^4$; or a phenyl group optionally substituted with one or more groups represented by $R^5$;

each $R^5$ is independently selected from halo; alkyl; —$OR^a$; alkoxy; haloalkoxy; —CHO; —$COOR^b$; —COOR"; C(O)R"; —$NO_2$; haloalkyl; and —CN;

R' is an alkyl group; or a phenyl group optionally substituted with halo; —$OR^a$; alkoxy; haloalkoxy; —CHO; —$COOR^b$; —COOR"; C(O)R"; —$NO_2$; alkyl; haloalkyl; or —CN; and the remainder of the variables are as described above for Structural Formula (XII).

In another embodiment, the deuterated benzo[d][1,3]dioxole represented by Structural Formula (XIII):

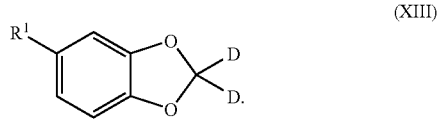

(XIII)

$R^1$ is —CHO or —$OR^a$; and $R^a$ is —H or a phenol protecting group.

In an alternative embodiment, the isotopic enrichment of the compounds represented by Structural Formulas (XIIa) and (XIII) is at least 96%, such as at least 97% and at least 98%, and all of the structural variables are as described above.

The structures of two particularly useful d₂-benzo[d][1,3]dioxoles prepared by the disclosed method are shown below:

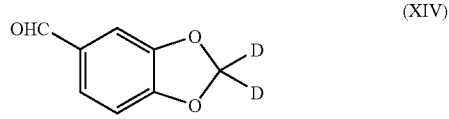

(XIV)

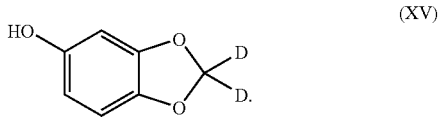

(XV)

The d₂-benzo[d][1,3]dioxole represented by Structural Formula (XIV) is used in the preparation of deuterated tadalafil (XIX, $R^1$=H, $R^2$=CD$_3$) and of deuterated berberine (XXI, X=Cl) (see Scheme 3); and the d₂-benzo[d][1,3]dioxole represented by Structural Formula (XV) is used in the preparation of deuterated paroxetines XVII (see Scheme 1) and XVIII (see Scheme 7). Details of suitable experimental conditions follow.

Another embodiment of the invention is a deuterated paroxetine, a deuterated tadalafil or a pharmaceutically acceptable salt of the deuterated paroxetine or the deuterated tadalafil. The deuterated paroxetine, deuterated tadalafil or pharmaceutically acceptable salt of the deuterated paroxetine or the deuterated tadalafil comprise a benzo[d][1,3]dioxole group represented by Structural Formula (XVI):

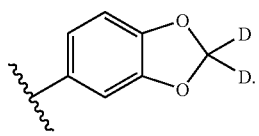

(XVI)

In Structural Formula (XVI) (and other Structural Formulas having the benzo[d][1,3]dioxole group), the carbon bearing the deuterium is referred to as the methylenedioxy carbon. The isotopic enrichment of the benzo[d][1,3]dioxole group represented by structural Formula (XVI) with deuterium is at least 99.0%, typically at least 99.5% and more typically at least 99.9%. The 99.0% isotopic enrichment with deuterium of the benzo[d][1,3]dioxole group represented by structural Formula (XVI) means that there are at least 0.990 moles of deuterium at each site designated as having deuterium per mole of benzo[d][1,3]dioxole for a total of at least 0.990×2 moles of deuterium atoms in the benzo[d][1,3]dioxole group per mole of benzo[d][1,3]dioxole group.

In other words, 99% isotopic enrichment with deuterium of the benzo[d][1,3]dioxole group represented by Structural Formula (XVI) means that with respect to each designated deuterium atom in the structure, at least 99.0% of the molecules of a compound represented by the structure will have that deuterium atom present.

Examples of deuterated paroxetine and deuterated tadalafil of the present invention are represented by Structural Formulas (XVII)-(XIX):

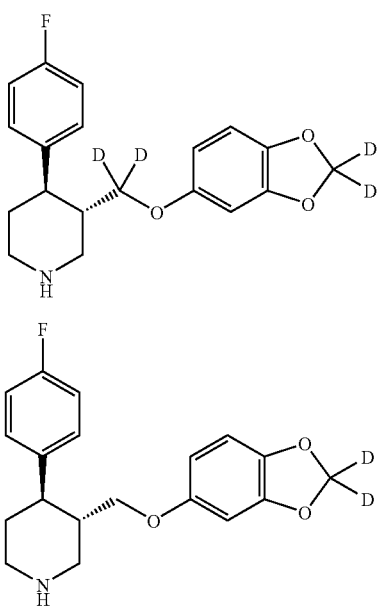

(XVII)

(XVIII)

-continued

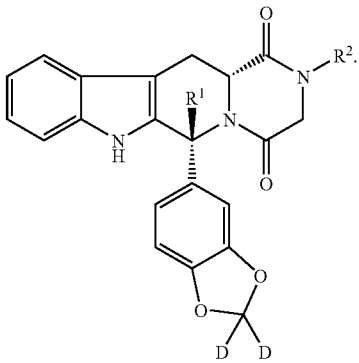

(XIX)

$R^1$ is H or D and $R^2$ is —$CH_3$ or —$CD_3$. Pharmaceutically acceptable salts of deuterated paroxetine represented by Structural Formulas (XVII) and (XVIII) and deuterated tadalafil represented by Structural Formula (XI) are also included.

In an alternative embodiment, the isotopic enrichment of the compounds represented by Structural Formulas (XIV), (XV), (XVI), (XVII), (XVIII), (XIX), (XX) and (XXI) is at least 96%, such as at least 97% and at least 98%, and all of the structural variables are as described above for the given Structural Formula.

In a particular set of embodiments, any atom not designated as deuterium in Structural Formulas: II, III, IV, IVa, IVb, V, Va, Vb, VII, IX, XI, XII, XIIa, XIII, XIV, XV, XVI, XVII, XVIII, XIX, XX, and XXI, is present at its natural isotopic abundance.

Synthetic details for incorporating deuterium into the labeled sites shown in Structural Formulas (XVII)-XIX) that are outside of the benzo[d][1,3]dioxole group are provided in WO 2007/016431, US2007/0112031 and US2007/0191381, the entire teachings of which are incorporated herein by reference.

Another embodiment of the invention is a deuterated berberine. The deuterated berberine comprises a benzo[d][1,3]dioxole group represented by Structural Formula (XX):

(XX)

The isotopic enrichment of the benzo[d][1,3]dioxole group represented by Structural Formula (XX) with deuterium is at least 99.0%, typically at least 99.5% and more typically at least 99.9%. The 99.0% isotopic enrichment with deuterium of the benzo[d][1,3]dioxole group represented by Structural Formula (XX) means that there are at least 0.990 moles of deuterium at each site designated as having deuterium per mole of benzo[d][1,3]dioxole for a total of at least 0.990×2 moles of deuterium atoms in the benzo[d][1,3]dioxole group per mole of benzo[d][1,3]dioxole group.

An example of a deuterated berberine of the present invention is represented by Structural Formula (XXI):

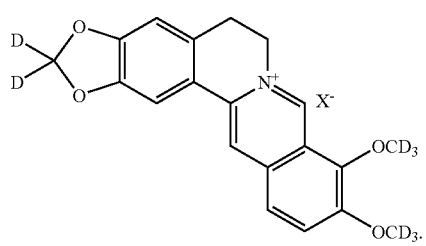

(XXI)

wherein X⁻ is a pharmaceutically acceptable anion.

When a deuterated compound of this invention is designated as having deuterium at a position other than at the benzo[d][1,3]dioxole group (e.g., the methoxy groups in Structural Formula (XXI)), the isotopic enrichment for each deuterium present at the designated site designated site is at least 15%, at least 22.5%, at least 30%, at least 37.5%, at least 45%, at least 52.5%, at least 60% deuterium, at least 67.5%, at least 75%, at least 82.5%, at least 90%, at least 95%, at least 97%, at least 99.0%, or at least 99.5%. It is understood that the isotopic enrichment of each deuterium present at a site designated as a site of deuteration is independent of other deuterated sites.

Included in the invention are pharmaceutically acceptable salts of the deuterated paroxetine and deuterated tadalafil compounds disclosed herein. These disclosed compounds have basic amine groups and therefore can form pharmaceutically acceptable salts with pharmaceutically acceptable acid(s). Suitable pharmaceutically acceptable acid addition salts of the compounds of the invention include salts of inorganic acids (such as hydrochloric, hydrobromic, phosphoric, metaphosphoric, nitric, and sulfuric acids) and of organic acids (such as, acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds with a quaternary ammonium group (such as berberine) also contain a counteranion such as chloride, bromide, iodide, acetate, perchlorate and the like or the anion of any one of the aforementioned acids. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "alkyl" as used herein means a saturated straight-chain or branched hydrocarbon having one to ten carbon atoms, more typically one to six; or a saturated cyclic hydrocarbon having three to eight carbon atoms.

The term "aryl group" means carbocyclic aromatic rings have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl.

Ring A in Structural Formulas (I) and (II) comprises substituents which do not interfere with the reactions described therein. Specifically, substituents that are sufficiently acidic that they react with the base used in the Alkylation Reaction are desirably derivatized with a suitable protecting group. Examples of substituents of this type include carboxylic acids, sulfonic acids, alcohols and phenols. Additionally, substituents that are sufficiently nucleophilic that they can react with the dihalodideuteromethane are also desirably derivatized with a suitable protecting group. Examples of substituents of this type include primary and secondary amines, phenols and alcohols.

"Protecting groups" and reactions and conditions for protecting and deprotecting the phenol group are well known in the art and are disclosed, for example, in Greene and Wuts, "Protective Groups in Organic Synthesis", John Wiley & Sons (2007), Chapter 2 and references cited therein.

Suitable protecting groups protect the phenol group as ethers, examples of such protecting groups include methyl, methoxymethyl, methylthiomethyl, (phenyldimethylsilyl) methoxymethyl, benzyloxymethyl, p-methoxybenzyloxymethyl, [3,4-dimethoxybenzyl)oxy]methyl, p-nitrobenzyloxymethyl, o-nitrobenzyloxymethyl, [(R)-1-(2-nitrophenyl) ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy) methyl, 2,2,2-trichloroethoxymethyl, 2-(trimethylsilyl) ethoxymethyl, menthoxymethyl, o-bis(2-acetoxyethoxy) methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl, S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahyrdo-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1,-dianisyl-2,2,2,-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-(phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorosbenzyl, 4-fluorousalkoxybenzyl, trimethylsilylxylyl, p-phenylbenzyl, 2-phenyl-2-propyl (cumyl), p-acylaminobenzyl, p-azidobenzyl, 4-azido-3-chlorobenzyl, 2- and 4-trifluoromethylbenzyl, p-(methylsulfinyl)benzyl, p-siletanylbenzyl, 4-acetoxybenzyl, 4-(2-trimethylsilyl) ethoxymethoxybenzyl, 2-naphthylmethyl, 2- and 4-picolyl, 3-methyl-2-picolyl N-oxide, 2-quinolinylmethyl, 6-methoxy-2-(4-methylphenyl)-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"tris(benzoyloxyphenyl) methyl, 4,4'-dimethoxy-3"-[N-(imidazolylmethyl)trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i] fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, 4,5-bis (ethoxycarbonyl-[1,3]-dioxolan-2-yl, benzisothiazolyl S,S-dioxido, trimethylsilyl, triethylsilyl, triisopropylsilyl, dimethylisopropylsiyl, diethylisopropylsilyl, dimethylthexylsilyl, 2-norbornyldimethylsily, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, sisyl, (2-hydroxystyryl)dimethylsilyl, (2-hydroxystyryl)diisopropylsilyl, t-butylmethoxyphenylsilyl, t-butoxydiphenylsilyl and 1,1,3,3-tetraisopropyl-3-[2-(triphenylmethoxy)ethoxy]disiloxane-1-yl.

Alternatively, suitable protecting groups protect the phenol group as esters, for example, formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, p-phenylacetate, diphenylacetate, 3-phenylpropionate, bisfluorous chain type propanoyl (Bfp-OR), 4-pentenoate, 4-oxopentanoate (levulinate), 4,4-(ethylenedithio)pentanoate, 5-[3-Bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate (mesitoate), 4-bromobenzoate, 2,5-difluorobenzoate, p-nitrobenzoate, picolinate, nicotinate, 2-(azidomethyl)benzoate, 4-azidobutyrate, (2-azidomethyl) phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2{{[4-methoxytrityl)thio]methylamino}-methyl}benzoate, 2-(allyloxy)phenylacetate, 2-(prenyloxymethyl)benzoate, 6-(levulinyloxymethyl)-3-methoxy-2- and 4-nitrobenzoate, 4-benzyloxybutyrate, 4-trialkylsiloxybutrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-methylthiomethoxy)butyrate, 2-methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy) ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate tigloate), o-(methoxycarbonyl)benzoate, p-benzoate, α-naphthoate, nitrate, alkyl N,N,N',N'-tetramethylphosphorodiamidate, 2-chlorobenzoate, as sulfonates, sulfenates and sulfinates such as sulfate, allylsulfonate, ethanesulfonate (mesylate), benzylsulfonate, tosylate, 2-[(4-nitrophenyl)ethyl]sulfonate, 2-trifluoromethylsulfonate, 4-monomethoxytritylsulfenate, alkyl 2,4-initrophenylsulfenate, 2,2,5,5-tetramethylpyrrolidin-3-one-1-sulfinate, borate, dimethylphosphinothioyl, as carbonates such as alkyl methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(-methoxytrityl)sulfenyl]oxy]tetraydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxyl-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-yl methyl carbonate, 2-dansylethyl carbonate, 2-(4-nitrophenyl)ethyl, 2-(2,4-nitrophenyl)ethyl, 2-(2-nitrophenyl)propyl, 2-(3,4-methylenedioxy-6-nitrophenylpropyl, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, S-benzyl thiocarbonate, and carbamates such as dimethylthiocarbamate, N-phenylcarbamate, and N-methyl-N-(o-nitrophenyl) carbamate.

Examples of suitable protecting groups for amino groups include carbamates (e.g, methyl, ethyl, 9-fluorenylmethyl, 9-(2-sulfo)fluorenylmethyl, 9-(2,7-dibromo)fluorenylmethyl, 17-tetrabenzo[a,c,g,i]fluoernylthmethyl, 2-chloro-3-indenylmethyl, benzo[f]inden-3-ylmethyl-2,7-di-t-butyl-[9-(10,10-dioxo-10,10,10,10-tetrahydrothioxanthyl)]methyl, 1,1-dioxobenzo[b]thiophene-2-ylmethyl, 2,2,2-tricholoroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2-dibromoethyl, 1,1-dimethyl-2,2,2-trichloroethyl, 1-methyl-1-(4-biphenylyl)ethyl, 1-(3,5-di-t-butylphenyl)-1-methylethyl, t-butyl, 1-adamantyl, 2-adamantyl, vinyl, allyl, 1-isopropylallyl, cinnamyl, 4-nitrocinnamyl, benzyl, p-methoxybenzyl, p-nitrobenzyl, p-bromobenzyl, p-chlorobenzyl, 2,4-dichlorobenzyl, m-nitrophenyl, 3,5-dimethoxybenzyl, 1-methyl-1-(3,5-dimethoxyphenyl)ethyl, α-methylnitropiperonyl, o-nitrobenzyl, 3,4-dimethoxy-6-nitrobenzyl, and phenyl(o-nitrophenyl)methyl), amides (e.g., n-formyl, n-acetyl, n-chloroacetyl, n-trichloroacetyl, n-trifluoroacetyl, n-phenylacetyl, and n-3-phenylpropionyl), N-alkyl and N-aryl amines (e.g., n-methyl, n-t-butyl, n-allyl, n-benzyl, n-4-methoxybenzyl, n-2,4-dimethoxybenzyl, and n-2-hydroxybenzyl).

Examples of suitable protecting groups for carboxylic acid groups include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl, α-methylphenacyl, p-methoxyphenacyl, desyl, carboxamidomethyl, p-azobenzenecarboxamidomethyl, N-phthalimidomethyl, 2,2,2-trichloroethyl, 2-haloethyl, co-chloroalkyl, 2-(trimethylsilyl)ethyl, 2-methylthioethyl, 1,3-dithianyl-2-methyl, 2-(p-nitropheylsulfenyl)ethyl, 2-(p-toluenesulfonyl)ethyl, 2-2'-pyridyl)ethyl, 2-(p-methoxyphenyl) ethyl, 2-(diphenylphosphino)ethyl, 1-methyl-1-phenylethyl, 2-(4-acetyl-2-nitrophenyl)ethyl, 2-cyanoethyl, t-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(Prenyl), 3-buten-1-yl, 4-(trimethylsilyl)-2-buten-1-yl, cinnamyl, α-methylcinnamyl, prop-2-ynyl (Propargyl), phenyl, 2,6-dimethylphenyl, 2,6-diisopropylphenyl, 2,6-di-t-butyl-4-methylphenyl, 2,6-di-t-butyl-4-methoxyphenyl, p-(methylthio)phenyl, pentafluoropheynyl, benzyl, triphenylmethyl, diphenylmethyl, bis(o-nitrophenyl) methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxocyclohexylidene)-3-methylbutyl]amino}benzyl, piperonyl, 4-picolyl, p-benzyl, trimethylsilyl, triethylsilyl, t-butyldimethylsilyl, i-propyldimethylsilyl, phenyldimethylsilyl, di-t-butylmethylsilyl and triisopropylsilyl.

The structural formulas depicted herein designate certain atoms as sites enriched with deuterium (e.g., the phenolic groups in Structural Formula (II)), but do not designate other positions. In a most general embodiment, when a structural formula is silent with respect to whether a particular position is isotopically enriched, it is to be understood that the stable isotopes at the particular position are present either at natural abundance, or alternatively, that the particular position is isotopically enriched with one or more naturally occurring stable isotopes. In a more specific embodiment, the stable isotopes are present at natural abundance at all positions in a compound not designated as potential sites of isotopic enrichment (referred to herein as "non-designated atoms).

While this invention has been particularly shown and described with references to example embodiments thereof, it will be understood by those skilled in the art that various changes in form and details may be made therein without departing from the scope of the invention encompassed by the appended claims.

Exemplary Syntheses Using Dideutero Benzo[d][1,3]Dioxoles

The following schemes outlining the preparation of $d_4$-paroxetine, $d_2$- and $d_3$-tadalafil, and $d_8$-berberine are given as examples where the dideutero benzo[d][1,3]dioxole intermediates XIV and XV could be used.

$D_4$-Paroxetine Synthesis

The synthesis of $d_4$-paroxetine (XVII) also known as (3S, 4R)-3-((2,2-$d_2$-benzo[d][1,3]dioxol-5-yloxy)methyl-$d_2$)-4-(4-fluorophenyl)piperidine hydrochloride using intermediate XV is outlined in Scheme 1 below. Details of the synthetic procedure are provided and are based on the actual preparation of $d_4$-paroxetine, that was performed without the benefit of the high isotopically enriched intermediate XV. One of ordinary skill in the art would recognize that the same procedures can be performed using an intermediate XV of this invention to provide $d_4$-paroxetine having high isotopic enrichment of the methylenedioxy carbon position.

Scheme 1.

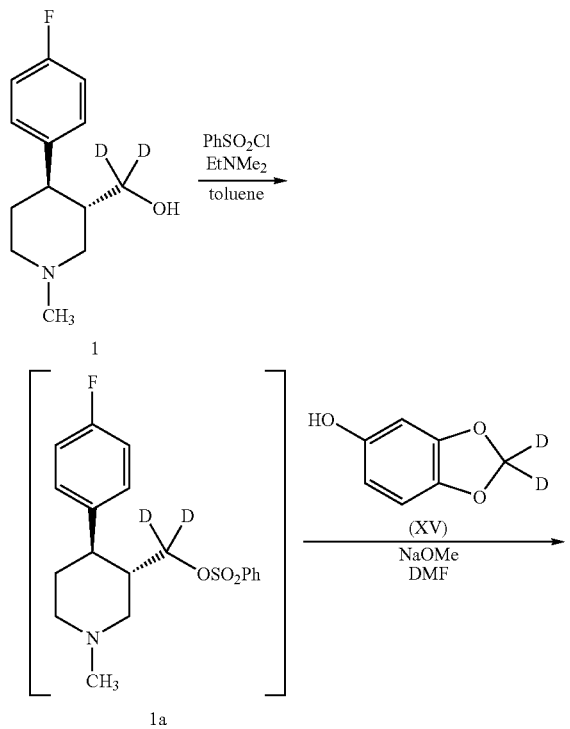

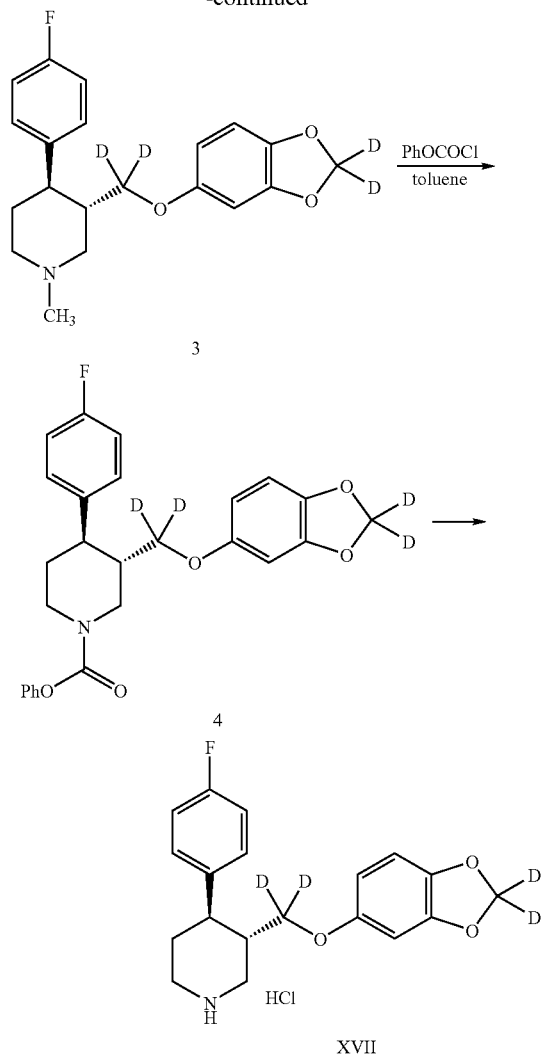

Synthesis of (3S,4R)-3-((2,2-$d_2$-benzo[d][1,3]dioxol-5-yloxy)methyl-$d_2$)-4-(4-fluorophenyl)-1-methylpiperidine (3)

To a solution of ((3S,4R)-4-(-4-fluorophenyl)-1-methylpiperidin-3-yl)methanol-$d_2$ (1) in toluene at 5° C., can be added dimethylethylamine with stirring. A nitrogen purge can be attached and the mixture can be further cooled to 0° C. A mixture of benzenesulphonyl chloride in toluene can be added slowly over 70 minutes (min), maintaining the temperature at around 0° C. The resulting mixture can be stirred for 20 minutes, allowing the temperature to rise to 10° C. A mixture of saturated brine and aqueous sodium hydroxide can be added over 10 min and the resulting mixture can be stirred for 15 min at 10° C. The aqueous phase can be separated, and extracted with toluene. The combined toluene phases can be dried over anhydrous magnesium sulfate, filtered and approximately one third of the solvent can be removed in vacuo. This solution of intermediate 1a can be diluted with N,N'-dimethylformamide, the resulting mixture can be warmed to 50° C., and a solution of XV and sodium methoxide (9.33 g) in N,N'-dimethylformamide can be added over 20 min. Water can be added and the mixture can be heated to 70° C., then stirred at that temperature for 1 hour (h). After cooling to 50° C., more water can be added, and stirring can be continued for 15 minutes. The aqueous phase can be separated and extracted with toluene. The combined toluene phases are washed with 2.5 molar aqueous sodium hydroxide solution (2 times) and water (1 times). The resulting toluene phase can be then dried over anhydrous magnesium sulfate (10.4 g) and filtered. Toluene can be removed by distillation at reduced pressure to form 3 as a pale yellow solid, which can be dried in a vacuum oven (40° C.) overnight.

Synthesis of (3S,4R)-phenyl-3-((2,2-$d_2$-benzo[d][1,3]dioxolo-5-yloxy)methyl-$d_2$)-4-(4-fluorophenyl)piperidine-1-carboxylate (4)

A solution of the methylpiperidine (3) in dry toluene can be heated to 60-65° C. and phenyl chloroformate can be added over 15 minutes with stirring. The resulting mixture can be stirred for 1 h at 60-65° C., then can be cooled to 20° C. and washed with 10% aqueous (aq) sulphuric acid. The combined acid washes are extracted with toluene and the combined organic phases are washed with water, dried over magnesium sulfate, and filtered over Celite. The filtrate can be concentrated in vacuo followed by the addition of propan-2-ol; this concentration/redissolution step can be repeated 2 times. After the last dissolution with propan-2-ol, the solution can be slowly cooled to 0 to 5° C. over 2 h and then stirred at this temperature for about 1 h, to provide the product as crystals. The crystals are isolated by filtration, and dried to yield product 4.

Synthesis of (3S,4R)-3-((2,2-$d_2$-benzo[d][1,3]dioxol-5-yloxy)methyl-$d_2$)-4-(4-fluorophenyl)piperidine hydrochloride (XVII)

A suspension of 4 (0.8 mmol) in 3 N KOH (0.37 mL) can be heated at reflux for 4 h. The mixture can be cooled and partitioned between 10 mL each of water and methylene chloride. The aqueous portion can be separated, extracted with methylene chloride and the combined organic layers are washed with 50% brine, dried over $MgSO_4$ and concentrated in vacuo. The residue can be taken up in 2 mL of isopropyl alcohol and treated with 0.9 mmol of anhydrous HCl as a 4.2 N solution in dioxane. The resulting solid can be filtered, washed with a small amount of isopropyl alcohol, then with ether, and dried to yield the desired product XVII.

Deuterated-Tadalafil Synthesis

The synthesis of $d_2$- or $d_3$-tadalafil using intermediate XIV can be carried out as outlined in Scheme 2 below.

Scheme 2.

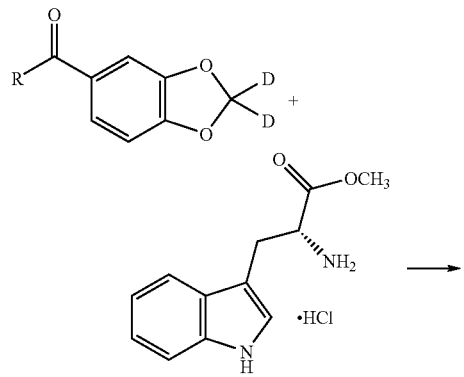

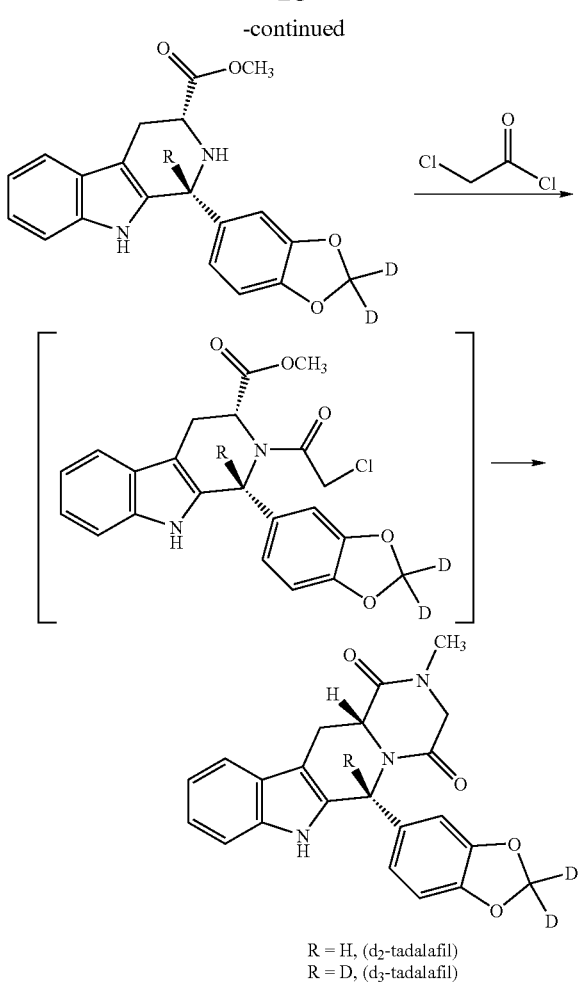

R = H, ($d_2$-tadalafil)
R = D, ($d_3$-tadalafil)

$D_8$-Berberine Synthesis

The synthesis of $d_8$-berberine (XXI, where X=Cl) also known as 5,6-dihydro-9,10-(dimethoxy-$d_6$)-benzo[g]-(2,2-$d_2$-benzo[d][1,3]dioxolo[5,6-a]quinolizinium chloride using intermediate XIV is outlined in Scheme 3 below. Details of a synthetic procedure are provide and are based on the actual preparation of dg-berberine that was performed without the benefit of the high isotopically enriched intermediate XIV. One of ordinary skill in the art would recognize that the same procedures can be performed using an intermediate XIV of this invention to provide $d_4$-paroxetine having high isotopic enrichment of the methylenedioxy carbon position.

Scheme 3.

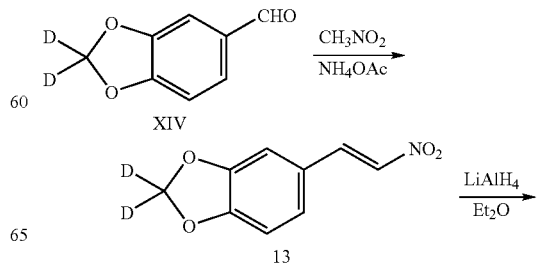

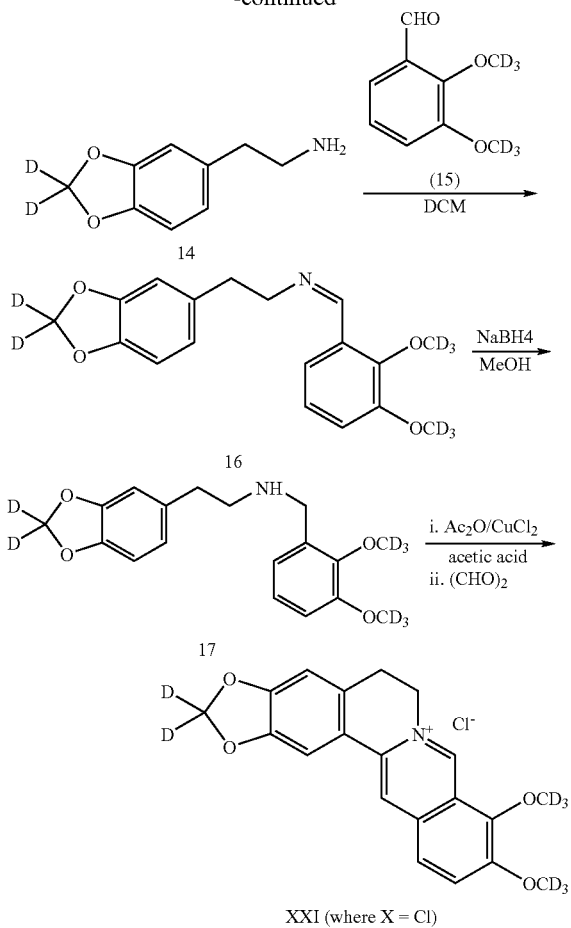

Synthesis of (E)-5-(2-nitrovinyl)-2,2-d$_2$-benzo[d][1,3]dioxole (13)

A mixture of XIV (85.4 g, 0.562 mol, 1.0 eq.), nitromethane (91.0 mL, 1.68 mol, 3.0 eq.) and ammonium acetate (108.2 g, 1.40 mol, 2.5 eq.) in acetic acid (500 mL) can be stirred under reflux conditions for 4 h. After cooling to rt, the mixture can be poured into ice-water (500 mL) and extracted with dichloromethane (DCM) (3×1.4 L). The dichloromethane solution can be washed with water (2×1.4 L) and brine (2×1.4 L), dried (MgSO$_4$), filtered and concentrated in vacuo to yield the crude product as a brown oil which can be purified by column chromatography, (SiO$_2$; 1:1 DCM/hexane) to give 13.

Synthesis of 2-(2,2-d$_2$-benzo[d][1,3]-dioxol-5-yl) ethanamine (14)

A solution of 13 (62.1 g, 0.318 mol, 1 eq.) in THF (1.28 L) can be added dropwise to a well stirred suspension of LiAlH$_4$ (45.9 g, 1.21 mol, 3.8 eq.) in Et$_2$O (1.9 L). The mixture can be heated to reflux for 2 h, after which time the reaction should be complete. The solution can be cooled in an ice bath and quenched by the dropwise addition of water (46 mL), followed by the addition of a 15% aqueous NaOH solution (46 mL) and more water (138 mL). The mixture can be allowed to stir for 30 min. then filtered and the organic solvents removed in vacuo. The aqueous residue can be extracted with DCM (3×900 mL) and the combined organics extracted with 5% aqueous HCl (640 mL). The acidic aqueous layer can be basified to pH 9 with 5% aqueous NH$_4$OH (640 mL), extracted with DCM (3×900 mL) and the combined organics washed with water (2×900 mL) and brine (2×900 mL), dried (MgSO$_4$), filtered and concentrated in vacuo to give 14.

Synthesis of (Z)-2-(2,2-d$_2$-benzo[d][1,3]dioxol-5-yl)-N-(2,3-(dimethoxy-d$_6$)-benzylidene)ethanamine (16)

A mixture of the amine 14 (21.55 g, 0.129 mol, 1.0 eq.), the aldehyde 15 (22.20 g, 0.129 mol, 1.0 eq.) and 4 Å molecular sieves (63.0 g) in anhydrous DCM (600 mL) can be stirred at room temperature for 16 h, until the reaction can be complete. The mixture can be filtered through Celite (100 g) and the DCM removed in vacuo to give the crude product 16.

Synthesis of 2-(2,2-d$_2$-benzo[d][1,3]dioxol-5-yl)-N-(2,3-(dimethoxy-d$_6$)benzyl)ethanamine (17)

A mixture of the imine 16 (40.4 g, 0.126 mol, 1.0 eq.) and sodium borohydride (7.15 g, 0.189 mol, 1.5 eq.) in methanol (450 mL) can be heated at reflux with stirring for 2 h. The reaction can be cooled to 0 and 5° C. (ice-bath), and water (450 mL) can be added. The mixture can be extracted with DCM (2×900 mL), and the combined organics were dried (MgSO$_4$), filtered and concentrated in vacuo to give the product 17.

The free base (38.2 g, 0.118 mol, 1.0 eq.) can be dissolved in methanol (240 mL) and conc. HCl (10 mL) can be added until pH 4 is obtained. The solvents can be removed in vacuo to give a brown oil which can be cooled to 0° C. with stirring and cold Et$_2$O/MeOH (4:1, 48 mL) can be added. The mixture can be stirred for 30 min resulting in the formation of a solid which can be filtered off. Further cold Et$_2$O/MeOH (4:1, 48 mL) can be added to the filtrate which can be stirred for 20 min, resulting in the formation of additional solid. The solid can be removed by filtration and the combined solids are washed with cold Et$_2$O and dried to give the HCl salt 17.

Synthesis of 5,6-dihydro-9,10-(dimethoxy-d$_6$)-benzo[g]-(2,2-d$_2$-benzo[d][1,3]dioxolo[5,6-a]quinolizinium chloride (XXI, where X═Cl)

A 250 mL dry three-necked flask can be charged with acetic anhydride (13.9 g, 0.136 mol, 2.5 eq), acetic acid (100 mL), CuCl$_2$ (14.7 g, 0.109 mol, 2.0 eq) and NaCl (13.8 g, 0.240 mol, 4.4 eq). The mixture can be heated to 80 and 90° C., glyoxal (40% in water, 13.4 g, 0.725 mol, 1.5 eq) can be added and the mixture can be heated at reflux for 20 minutes. The mixture can be cooled to less than 90° C., and the amine HCl salt 17 (19.7 g, 0.055 mol, 1.0 eq) can be added, and the mixture heated to reflux (112-114° C.) with stirring overnight. The reaction mixture can be cooled to 50° C. and the acetic acid can be distilled off under reduced pressure. The residue can be charged with water (170 mL) and the mixture heated to 80° C. with stirring for 20 minutes. The salt XXI can be obtained by filtration, then can be added to aqueous ammonium hydroxide (0.72 M, 550 mL) and the mixture can be stirred at 25 to 30° C. for 2.5 h. The solid can be again filtered, washed with cold water (110 mL), and dried overnight in vacuo at 40° C. to afford crude product.

The crude product can be dissolved in MeOH (800 mL), stirred at reflux for 30 min then filtered hot to give a dark brown solid (12.1 g). The solid can be suspended in MeOH (1 L), stirred at reflux for 30 min then filtered hot to give a dark brown solid (10.2 g). The two filtrates are combined, charcoal (12.0 g) can be added and the mixture heated at just below reflux for 20 min then the hot suspension can be filtered through Celite. The filtrate can be concentrated in vacuo to give an orange solid which can be recrystallised from MeOH (104 mL, 16 vols), yielding XXI.

Compositions

The invention also provides compositions comprising an effective amount of a deuterated paroxetine, deuterated tadalafil, or deuterated berberine, as described herein, or a pharmaceutically acceptable salt thereof; and an acceptable carrier. The carrier(s) must be "acceptable" in the sense of being compatible with the other ingredients of the formulation.

In a particular embodiment, the invention provides a composition comprising deuterated paroxetine or a pharmaceutically acceptable salt thereof, comprising a benzo[d][1,3]dioxole group represented by the following structural formula:

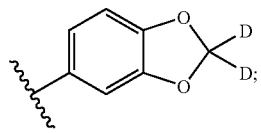

wherein the isotopic enrichment of the benzo[d][1,3]dioxole group with deuterium is at least 99.0%; and a pharmaceutically acceptable carrier, and wherein said composition is formulated for pharmaceutical use ("a pharmaceutical composition"). A "pharmaceutically acceptable carrier" is a carrier that is compatible with the other ingredients of the composition and not deleterious to the recipient thereof in amounts typically used in medicaments. In a more particular embodiment, the isotopic enrichment is at least 99.5%. In an even more particular embodiment, the isotopic enrichment is 99.9%.

In another embodiment, the invention provides a composition comprising deuterated paroxetine or a pharmaceutically acceptable salt thereof, represented by the following structural formula:

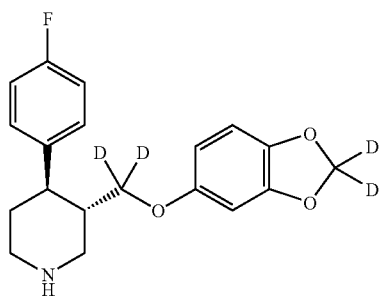 [SMILES: [2H]C1([2H])Oc2ccc(OC([2H])([2H])[C@@H]3CNCC[C@H]3c3ccc(F)cc3)cc2O1]

wherein the isotopic enrichment of the benzo[d][1,3]dioxole group with deuterium is at least 99.0%; and a pharmaceutically acceptable carrier, and wherein said composition is formulated for pharmaceutical use ("a pharmaceutical composition").

In another embodiment, the invention provides a composition comprising deuterated paroxetine or a pharmaceutically acceptable salt thereof, represented by the following structural formula:

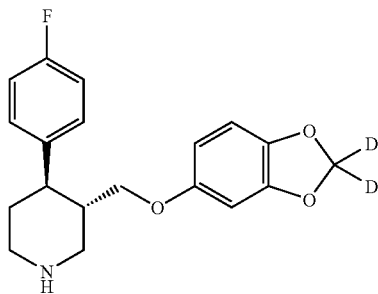 [SMILES: [2H]C1([2H])Oc2ccc(OC[C@@H]3CNCC[C@H]3c3ccc(F)cc3)cc2O1]

wherein the isotopic enrichment of the benzo[d][1,3]dioxole group with deuterium is at least 99.0%; and a pharmaceutically acceptable carrier, and wherein said composition is formulated for pharmaceutical use ("a pharmaceutical composition").

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compounds disclosed herein may be administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. Surfactants such as sodium lauryl sulfate may be useful to enhance dissolution and absorption.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be administered in the form of suppositories for rectal or vaginal administration. These compositions can be prepared by mixing deuterated paroxetine, deuterated tadalafil or detuerated berberine, as described herein, or a pharmaceutically acceptable salt thereof with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition will be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches and iontophoretic administration are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Such administration is known to be effective with erectile dysfunction drugs: Rabinowitz J D and Zaffaroni A C, U.S. Pat. No. 6,803,031, assigned to Alexza Molecular Delivery Corporation.

In one particular embodiment, the pharmaceutical compositions of this invention may be formulated for controlled release upon oral dosing. Such controlled-release compositions are well-known in the art and are exemplified by the formulation of Paxil® CR™ (paroxetine hydrochloride controlled-release tablets), and as disclosed in PCT Patent publications WO2007015270, WO2007011139, WO2006123364, WO2006059866, WO 2005117839, WO 2005107716, and WO 1997003670.

Application of the subject therapeutics may be local, so as to be administered at the site of interest. Various techniques can be used for providing the subject pharmaceutical compositions at the site of interest, such as injection, use of catheters, trocars, projectiles, pluronic gel, stents, sustained drug release polymers or other device which provides for internal access.

Thus, according to another embodiment, deuterated paroxetine, deuterated tadalafil or detuerated berberine, as described herein, or a pharmaceutically acceptable salt thereof may be incorporated into a pharmaceutical composition for coating an implantable medical device, such as prostheses, artificial valves, vascular grafts, stents, or catheters. Suitable coatings and the general preparation of coated implantable devices are described in U.S. Pat. Nos. 6,099, 562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings are optionally further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating or filling an implantable drug release device comprising the step of contacting said drug release device with deuterated paroxetine or a pharmaceutical composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with deuterated paroxetine or a pharmaceutical composition of this invention, such that said compound is therapeutically active.

According to another embodiment, the invention provides an implantable drug release device impregnated with or containing deuterated paroxetine or a pharmaceutical composition of this invention, such that said compound is released form said device and is therapeutically active.

Where an organ or tissue is accessible because of removal from the patient, such organ or tissue may be bathed in a medium containing a pharmaceutical composition of this invention, a pharmaceutical composition of this invention may be painted onto the organ, or a pharmaceutical composition of this invention may be applied in any other convenient way.

For example, the present invention provides pharmaceutical compositions comprising an effective amount of deuterated paroxetine, deuterated tadalafil or deuterated berberine, as described herein, or a pharmaceutically acceptable salt thereof in combination with one or more second therapeutic agents and a pharmaceutically acceptable carrier. The present invention further provides pharmaceutical compositions comprising an effective amount of deuterated paroxetine, as described herein, or a pharmaceutically acceptable salt thereof in combination with an effective amount of one or more second therapeutic agents useful for treating or preventing a condition selected from depression, hypertension, generalized anxiety disorder, phobias, posttraumatic stress syndrome, avoidant personality disorder, sexual dysfunction; eating disorders including bulimia, anorexia nervosa, and binge eating; obesity, chemical dependencies, cluster headache, migraine; pain, including neuropathic pain, diabetic nephropathy, post-operative pain, psychogenic pain disorders, and chronic pain syndrome; Alzheimer's disease, obsessive-compulsive disorder, panic disorder with or without agoraphobia, memory disorders, Parkinson's diseases, endocrine disorders, vasospasm, cerebellar ataxia, gastrointestinal tract disorders, negative symptoms of schizophrenia, premenstrual syndrome, Fibromyalgia Syndrome; urinary incontinence, including stress incontinence; Tourette's syndrome, trichotillomania, kleptomania, male impotence, cancer, chronic paroxysmal hemicrania and headache in a mammal, sleep-related breathing disorders, cognitive deficits due to aging, stroke, head trauma, neurodegenerative diseases, schizophrenia, anxiety, aggression and stress, disorders of thermoregulation, respiratory disease, bipolar disorder, psychosis, sleep disorder, mania, acute mania, bladder disorder, genitourinary disorder, cough, emesis, nausea, and psychotic disorders such as paranoia and manic-depressive illness, tic disorder, diabetic cardiomyopathy, diabetic retinopathy, cataracts, myocardial infarction, prolonged fatigue, chronic fatigue, chronic fatigue syndrome, premature ejaculation, dysphoria, post partum depression, social phobia, disruptive behavior disorders, impulse control disorders, borderline personality disorder, attention deficit disorders without hyperactivity, Shy-Drager Syndrome, cerebral ischemia, spinal cord trauma, Huntington's Chorea, amyotrophic lateral sclerosis, AIDS-induced dementia, muscular spasms, convulsions, perinatal hypoxia, hypoxia, cardiac arrest, hypoglycemic neuronal damage, ocular damage and retinopathy, brain edema, tardive dyskinesia and cerebral deficits subsequent to cardiac bypass surgery and grafting, affective disorders, mood disorders agoraphobia without history of panic disorder, an acute stress disorder, autism, dyskinesia, dysthymic disorder; obesity due to genetic or environmental causes, polycystic ovary disease, craniopharyngioma, Prader-Willi Syndrome, Froehlich's Syndrome, Type II diabetes, growth hormone deficiency, and Turner's Syndrome; excessive or undesired proinflammatory cytokine secretion or production, jet lag, insomnia, hypersomnia, nocturnal enuresis, restless-legs syndrome, vaso-occlusive events, hyperglycemia, hyperinsulinemia, hyperlipidemia, hypertriglyceridemia, diabetes, insulin resistance, impaired glucose metabolism, conditions of impaired glucose tolerance (IGT), conditions of impaired fasting plasma glucose, glomerulosclerosis, syndrome X, coronary heart disease, angina pectoris, vascular restenosis, endothelial dysfunction, impaired vascular compliance, or congestive heart failure.

Also within the scope of this invention are pharmaceutical compositions comprising an effective amount of deuterated paroxetine, or a pharmaceutically acceptable salt thereof; or a prodrug or a pharmaceutically acceptable salt of a prodrug thereof; or a solvate, hydrate, or polymorph thereof; in combination with an effective amount of a second therapeutic agent useful for reducing the side effects of paroxetine, for enhancing or potentiating the activity of paroxetine, for increasing the duration of pharmacological action of paroxetine or for which paroxetine reduces the undesirable side effects; and a pharmaceutically acceptable carrier.

Additional therapeutic agents useful in combination with the compounds of this invention include, but are not limited to: 5-$HT_{1A}$ antagonist or ligand; an $NK_1$-receptor antagonist; a serotonin receptor antagonist; 2-amino-4,5,6,7-tetrahydro-6-propylamino-benzothiazole (pramipexole), the (+)- or (−)-enantiomer thereof; a sulfamate anticonvulsant agent; a precursor or prodrug of serotonin, or an intermediate in the biosynthesis of serotonin; selective agonists and antagonists of one or both of the 5-$HT_{1A}$ and 5-$HT_{1D}$ receptors; a composition containing dimethylaminoethanol (DMAE), omega 3-fatty acids, betaine, oligomeric proanthocyanidins, folic acid, vitamins C, E, $B_{12}$, $B_6$, $B_5$ and beta-carotene and minerals (calcium, magnesium, zinc and selenium); naltrexone; cyclobenzaprine, or metabolites thereof; olanzapine; olanzapine-N-oxide; 2-hydroxymethylolanzapine; an atypical antipsychotic; tramadol; an aldose reductase inhibitor, or a prodrug thereof; 1-threo-methylphenidate; a Type III, Type IV, mixed Type III-Type IV, or Type V phosphodiesterase inhibitor, or an ester, amide, prodrug, active metabolite, or combination thereof; a substituted indole estrogenic agent; (+)-1-(3,4-dichlorophenyl)-3-azabicyclo[3.1.0]hexane; folic acid; methyltetrahydrofolate; WAY 100635; betaxolol; (R)-3-N,N-dicyclobutylamino-8-fluoro-3,4-dihydro-2H-1-benzopyran-5-carboxamide hydrogen (2R,3R)-tartrate monohydrate; R-tofisopam; N-acetyl-serotonin; a DRD2-specific dopamine agonist; a $5HT_4$ receptor antagonist; nalmefene; moxonidine; mirtazapine; chromium; a cyclooxygenase-2 selective inhibitor; a $5HT_{2A}$ selective receptor antagonist; a $CB_1$ receptor antagonist; a MCH-1R receptor antagonist; a tetra-substituted pyrimidopyrimidine; a selective dopamine $D_4$ receptor ligand; trimebutine, fedotozine and mixtures thereof; an NMDA partial receptor agonist; an NMDA receptor antagonist; a cholinesterase inhibitor; a GSK-3 inhibitor; an alpha-2-delta ligand or a prodrug thereof; an extract of kava; a norepinephrine reuptake inhibitor; a corticosteroid; a non-steroidal immunophilin-dependent immunosuppressant; N-desmethylclozapine; an (R)-2,3-benzodiazepine as disclosed in US Patent Application 20040224943; a selective neuronal nitric oxide synthase inhibitor; modafinil; a selective oxytocin antagonist; a nicotine receptor antagonist; an adenosine A2a receptor antagonist; a 5-HT$_{2C}$ receptor antagonist; an AMPA receptor potentiator; a nicotine partial agonist; irindalone; a delta opioid receptor ligand; a growth hormone secretagogue; p-chloro-N-(2-morpholinoethyl)-benzamide and its metabolites; a Selective Estrogen Receptor Modulator (e.g., tamoxifen); a pharmaceutically acceptable salt of any of the said additional therapeutic agents; or combinations of two or more of the foregoing.

Examples of 5-HT$_{1A}$ antagonists and ligands include, but are not limited to, alprenolol, WAY 100135, WAY 100635, spiperone, pindolol, (S)-UH-301, penbutolol, propranolol, tertatolol; (R)-5-carbamoyl-8-fluoro-3-N,N-disubstituted-amino-3,4-dihydro-2H-1-benzopyran; and those disclosed in U.S. Pat. Nos. 5,776,969; 5,958,429; 6,136,861; 6,656,951; 6,780,860; 6,815,448; 6,821,981; 6,861,427; 6,894,053; and US Patent Application 20050085475.

Examples of NK$_1$-receptor antagonists include, but are not limited to, vestipitant, and those disclosed in U.S. Pat. Nos. 6,162,805; 6,878,732; US Patent Application 20050137208; as well as CNS-penetrant agents capable of inhibiting NK-1 receptor agonist-induced foot tapping in the gerbil, or attenuating separation-induced vocalizations by guinea-pig pups.

Examples of sulfamate anticonvulsant agents include, but are not limited to, topiramate and those disclosed in and referenced by U.S. Pat. No. 5,384,327.

Examples of precursors or prodrugs of serotonin, and intermediates in the biosynthesis of serotonin, include but are not limited to, L-tryptophan, L-5-hydroxytryptophan, diethyl N-benzyloxycarbonyl-5-benzyloxycarbonyloxy-L-tryptophyl-L-aspartate, dibenzyl N-benzyloxycarbonyl-5-hydroxy-L-tryptophanylaspartate, 5-Hydroxy-L-tryptophyl-L-aspartic acid trihydrate, diethyl N-benzyloxycarbonyl-5-hydroxy-L-tryptophyl-L-glutamate, diethyl 5-hydroxy-L-tryptophyl-L-glutamate hydrochloride, dibenzyl L-benzyloxycarbonyl-5-hydroxytryptophyl-L-glutamate, 5-hydroxy-L-tryptophyl-L-glutamic acid, pentachlorophenyl ester of N-benzyloxycarbonyl-5-hydroxy-L-tryptophan, methyl ester of N-benzyloxycarbonyl-5-hydroxy-L-tryptophyl-L-tyrosine, N-Acetyl-5-hydroxy-L-tryptophan, methyl ester of N-acetyl-5-hydroxy-L-tryptophyl-L-tyrosine, methyl ester of n-acetyl-5-hydroxy-L-tryptophyl-5-hydroxy-L-tryptophan, 5-hydroxy-L-tryptophyl-L-alanine hydrate, 5-hydroxy-L-tryptophan-L-valine, 5-hydroxy-L-tryptophyl-L-leucine, 5-hydroxy-L-tryptophyl-L-proline, 5-hydroxy-L-tryptophyl-L-phenylalanine, 5-hydroxy-L-tryptophyl-5-hydroxy-L-tryptophan, 5-hydroxy-L-tryptophyl-L-tryptophan, 1-5-hydroxytryptophyl-L-serine, 5-hydroxy-L-tryptophyl-L-arginine, 5-hydroxy-L-tryptophylglycine, 5-hydroxy 1-tryptophyl-gamma-aminobutyric acid, 5-hydroxy-L-tryptophanamide hydrate, methyl ester of 5-hydroxy-L-tryptophyl-L-histidine, benzyl ester of L-5-hydroxytryptophan, benzyl ester of N-benzyloxycarbonyl-5-hydroxy-L-tryptophyl-5-hydroxy-L-tryptophan, 5-Hydroxy-L-tryptophyl-5-hydroxy-L-tryptophan hemihydrate, 5-hydroxytryptophan inosinate, theophylline salt of (DL) 5-hydroxytryptophan, and combinations thereof.

Examples of atypical antipsychotic agents include, but are not limited to, risperidone, clozapine, seroquel, sertindole, ziprasidone, zotepine, olanzapine, iloperidone, Org 5222, melperone, amperozide, SM-9018, JL-13, quetiapine, and pharmaceutically acceptable salts thereof.

Examples of aldose reductase inhibitors include, but are not limited to, fidarestat, epalrestat, minalrestat, SPR-210, and zenarestat or zopolrestat, or a prodrug thereof.

Examples of selective agonists and antagonists of one or both of the 5-HT$_{1A}$ and 5-HT$_{1D}$ receptors include, but are not limited to, those disclosed in U.S. Pat. No. 6,562,813.

Examples of Type III phosphodiesterase inhibitors include, but are not limited to, bipyridines such as aminone, milrinone and olprinone; anagrelide, bemoradan, ibudilast, isomazole, lixazinone, motapizone, olprinone, phthalazinol, pimobendan, quazinone, siguazodan and trequinsin Examples of calcium channel blockers include, but are not limited to, amlodipine, diltiazem, felodipine, isradipine, nicardipine, nifedipine, and verapamil.

Examples of mixed type III-type IV phosphodiesterase inhibitors include, but are not limited to, anagrelide, bemoradan, ibudilast, isomazole, lixazinone, motapizone, olprinone, phthalazinol, pimobendan, quazinone, siguazodan and trequinsin.

Examples of type IV phosphodiesterase inhibitors include, but are not limited to, pyrrolidinones, in particular rolipram; quinazolinediones, xanthine derivatives, phenyl ethyl pyridines, tetrahydropyrimidones, diazepine derivatives, oxime carbamates, naphthyridinones, benzofurans, naphthalene derivatives, purine derivatives, imidazolidinones, cyclohexane carboxylic acids, benzamides, pyridopyridazinones, benzothiophenes, etazolate, S-(+)-glaucine, substituted phenyl compounds and substituted biphenyl compounds as further disclosed in U.S. Pat. No. 6,403,597.

Examples of type V phosphodiesterase inhibitors include, but are not limited to, sildenafil, vardenafil, tadalafil, zaprinast, dipyridamole, 3-isobutyl-8-(6-methoxy-isoquinolin-4-ylmethyl)-1-methyl-3,7-dihydro-purine-2,6-dione; and those disclosed in US Patent Applications 20030055070; 20040044005; 20030139429.

Examples of substituted indole estrogenic agents include, but are not limited to, those disclosed in and referenced by U.S. Pat. No. 6,369,051.

An example of a DRD2-specific dopamine agonist includes, but is not limited to, bromocriptine.

Examples of 5HT$_4$ receptor antagonists include, but are not limited to, A-85380, SB 204070, SB 207226, SB 207058, SB 207710, SB 205800, SB 203186, SDZ 205557, N 3389, FK 1052, SC 56184, SC 53606, DAU 6285, GR 125487, GR 113808, RS 23597, RS 39604, LY-353433 and R 50595.

Examples of cyclooxygenase-2 selective inhibitors include, but are not limited to, celecoxib, valdecoxib, deracoxib, rofecoxib, etoricoxib, tilmacoxib, cimicoxib, and those disclosed in and referenced by US Patent Applications 20050080084 and 20050085477.

Examples of 5-HT$_{2a}$ receptor antagonists include, but are not limited to, those disclosed and referenced by US Patent application 20050070577.

Examples of CB$_1$ receptor antagonists include, but are not limited to, rimonabant and those disclosed in and referenced by US Patent applications 20040248956, 20050009870, 20050014786, 20050054659, 20050080087, and 20050143381.

Examples of selective MCH-1R receptor antagonists include, but are not limited to, those disclosed in and referenced by US Patent applications 20050009815 and 20050026915.

Examples of tetra-substituted pyrimidopyrimidines include, but are not limited to, dipyridamole, mopidamol, dipyridamole monoacetate, 2,6-di-(2,2-dimethyl-1,3-dioxolan-4-yl)-methoxy-4,8-di-piperidinopyrimido-pyrimidine; 2,6-bis-(2,3-dimethyoxypropoxy)-4,8-di-piperidinopyrimidopyrimidine; 2,6-bis[N,N-di(2-methoxy)ethyl]-4,6-di-piperidinopyrimidopyrimidine-; and 2,6-bis(diethanolamino)-4,8-di-4-methoxybenzylaminopyrimidopyrimidine-.

Examples of selective dopamine D$_4$ receptor ligands include, but are not limited to, pipamperone, fananserin, L-745,870, PNU-101387G and U-101387.

An example of a NMDA partial receptor agonist includes, but is not limited to, D-cycloserine.

Examples of NMDA receptor antagonists include, but are not limited to, dextromethorphan, dextrorphan, amantadine, and memantine.

Examples of cholinesterase inhibitors include, but are not limited to, tacrine, donepezil, edrophonium, galantamine, physostigmine, eptastigmine, pyridostigmine, neostigmine, ganstigmine, rivastigmine, demecarium, ambenonium, sarin, metrifonate, soman, tabun, and diisopropyl fluorophosphates.

Examples of GSK-3 inhibitors include, but are not limited to, those disclosed and referenced in US Patent Application 20050026946.

Examples of alpha-2-delta ligands include, but are not limited to, gabapentin, pregabalin, [(1R,5R,6S)-6-(aminomethyl)bicyclo[-3.2.0]hept-6-yl]acetic acid, 3-(1-aminomethylcyclohexylmethyl)-4H-[1,2,4]-oxadiazol-5-one, C-[1-(1H-tetrazol-5-ylmethyl)-cycloheptyl]-methylamine, (3S,4S)-(1-aminomethyl-3,4-dimethylcyclopentyl)-acetic acid, (3-aminomethyl-bicyclo[3.2.0]hept-3-yl)-acetic acid, (3S,5R)-3-aminomethyl-5-methyloctanoic acid, (3S,5R)-3-amino-5-methylheptanoic acid, (3S,5R)-3-amino-5-methyl-nonanoic acid, and (3S,5R)-3-amino-5-methyloctanoic acid.

Examples of a norepinephrine reuptake inhibitors include, but are not limited to, desipramine, imipramine, amoxapine, nortriptyline, protriptyline, atomoxetine, oxaprotiline, maprotiline, reboxetine, 1-[1-(3-chlorophenyl)-2-(4-methyl-1-piperazinyl)ethyl]cyclohexanol; and those disclosed in US Patent Application 20050014848.

Examples of corticosteroids include, but are not limited to, prednisolone, budesonide, cortisone, dexamethasone, hydrocortisone, methylprednisolone, fluticasone, prednisone, triamcinolone, and diflorasone.

Examples of non-steroidal immunophilin-dependent immunosuppressants include, but are not limited to, cyclosporine, tacrolimus, ISAtx247, ascomycin, pimecrolimus, rapamycin, and everolimus.

Examples of selective neuronal nitric oxide synthase inhibitors include, but are not limited to, those disclosed in US Patent Application 20040229911.

An example of a selective oxytocin antagonist includes, but is not limited to, L-368,899.

Examples of nicotine receptor antagonists include, but are not limited to, mecamylamine, amantadine, pempidine, dihydro-beta-erythroidine, hexamethonium, erysodine, chlorisondamine, trimethaphan camsylate, tubocurarine chloride, d-tubocurarine, and their optical isomers.

Examples of adenosine A2a receptor antagonists include, but are not limited to, those disclosed in US Patent Application 20030139395.

Examples of 5-HT$_{2C}$ receptor antagonists, inverse agonists and partial agonists include, but are not limited to, ketanserin, SB 242084, SB 206553, SB 243213, SB 228356, ritanserin, deramciclane, mirtazepine, mianserine, sertindole, YM 35 992, Ro 60-0795, Org 38457, Org 12962, EGIS 8465 and RS 102221.

Examples of AMPA receptor potentiators include, but are not limited to, [(methylethyl)sulfonyl]{2-[4-(4-{2-[(methylsulfonyl)amino]ethyl}phenyl)phenyl]propyl}amine, {(2R)-2-[4-(4-{2-[(methylsulfonyl)amino]ethyl}phenyl)phenyl]propyl}[(methylethyl)sulfonyl]amine, N-2-(4-(3-thienyl)phenylpropyl-2-propanesulfonamide, [2-fluoro-2-(4-{3-[(methylsulfonyl)amino]phenyl}phenyl)propyl][(methylethyl)sulfonyl]amine, and, separately, each enantiomer of [2-fluoro-2-(4-{3-[(methylsulfonyl)amino]phenyl}phenyl)propyl][(methylethyl)sulfonyl]amine.

Examples of nicotine receptor partial agonists include, but are not limited to, those disclosed in US Patent Applications 20010036943 and 20030109544.

Examples delta opioid receptor ligands include, but are not limited to, those disclosed in and referenced by US Patent Application 20020077323.

Examples of growth hormone secretagogues include, but are not limited to, those disclosed in US Patent Applications 20020002137 and 20020086865.

In a more specific embodiment, the second therapeutic agent is selected from clozapine, vestipitant, quetiapine and naltrexone.

In another embodiment, the invention provides separate dosage forms of deuterated paroxetine, deuterated tadalafil or deuterated berberine, as described herein, or a pharmaceutically acceptable salt thereof and a second therapeutic agent, wherein said compound and said second therapeutic agent are associated with one another. The term "associated with one another" as used herein means that the separate dosage forms are packaged together in the same container (e.g., in separate blister packs attached to one another, in separate compartments of a compartmentalized container, in separate vessels contained in the same box, etc.), or otherwise attached to one another such that it is readily apparent that the separate dosage forms are intended to be sold and administered together (within less than 24 hours of one another, consecutively or simultaneously).

In the pharmaceutical compositions of the invention, deuterated paroxetine, deuterated tadalafil or deuterated berberine, or a pharmaceutically acceptable salt thereof is present in an effective amount. As used herein, the term "effective amount" refers to an amount which, when administered in a proper dosing regimen, is sufficient to treat (therapeutically or prophylactically) the target disorder. For example, an effective amount is sufficient to reduce or ameliorate the severity, duration or progression of the disorder being treated, prevent the advancement of the disorder being treated, cause the regression of the disorder being treated, enhance or improve the prophylactic or therapeutic effects of another therapy or reduce undesirable side effects associated with another therapy. For example, a pharmaceutical composition comprising and effective a deuterated paroxetine as described herein or a pharmaceutically acceptable salt thereof can enhance function compromised by a disorder associated with insufficient neurotransmission of serotonin, prevent the advancement of a disorder characterized by insufficient neurotransmission of serotonin, cause the regression of a disorder characterized by insufficient neurotransmission of serotonin, enhance or improve the prophylactic or therapeutic effect(s) of another therapy or reduce undesirable side effects of another therapy.

In certain preferred embodiments, treatment with a deuterated paroxetine, as described herein, or a pharmaceutically acceptable salt thereof provides a reduction in or prevention of at least one symptom or manifestation of a disorder that has been linked to insufficient neurotransmission of serotonin. With respect to inhibition of serotonin reuptake activity, the term "effective amount" means an amount that results in a detectable increase in the amount or concentration serotonin in a patient or in a biological sample, the correction of or relief from a behavior, deficit, symptom, syndrome or disease that has been linked to reduced or insufficient neurotransmission of serotonin, alone or in combination with another agent or agents; or the induction of a behavior, activity or response that has been linked to normalized or increased neurotransmission of serotonin.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardsley, N.Y., 1970, 537. An effective amount of deuterated paroxetine, as described herein, can range from about 0.001 mg/kg to about 500 mg/kg, more preferably 0.01 mg/kg to about 50 mg/kg, yet more preferably 0.025 mg/kg to about 1.5 mg/kg.

In another embodiment, an effective amount of deuterated paroxetine, as described herein, is greater than 60 mg/day and less than about 120 mg/day in an instant release formulation or greater than 75 mg/day and less than about 150 mg/day in a controlled release formulation. Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician.

In another embodiment, an effective amount of deuterated paroxetine is greater than 5 mg/day and less than about 65 mg/day in an instant release formulation, and more preferably greater than 7.5 mg/day and less than 80 mg/day in a controlled release formulation.

For pharmaceutical compositions that comprise a second therapeutic agent, an effective amount of that second therapeutic agent is between about 20% and 100% of the dosage normally utilized in a monotherapy regime using just that additional agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

It is expected that some of the second therapeutic agents listed above will act synergistically with the compounds of this invention. When this occurs, it will allow the effective dosage of the second therapeutic agent and/or deuterated paroxetine, as described herein, to be reduced from that required in a monotherapy. This has the advantage of minimizing toxic side effects of either the second therapeutic agent or deuterated paroxetine, synergistic improvements in efficacy, improved ease of administration or use and/or reduced overall expense of compound preparation or formulation.

Methods of Treatment

The terms ameliorate or treat are used interchangeably and include both therapeutic and prophylactic treatment. Both terms mean decrease, suppress, attenuate, diminish, arrest or stabilize the development or progression of a disease (e.g., a disease or disorder delineated herein), lessen the severity of the disease, improve the symptoms of the disease or improve side effects associated with other therapies.

Subject and patient are used interchangeably herein.

In one embodiment, the present invention provides a method of inhibiting the uptake of serotonin in a subject in need thereof comprising the step of administering to said subject an effective amount of deuterated paroxetine, as described herein, or a pharmaceutically acceptable salt thereof preferably as part of a composition additionally comprising a pharmaceutically acceptable carrier. This method can be employed to treat one or more disease or disorder in a subject in need thereof selected from depression; obsessive-compulsive disorder; generalized anxiety; post-traumatic stress; major depression; panic disorder; social phobia; pre-menstrual syndrome; cardiac disorders; non-cardiac chest pain; smoking addiction (to cause cessation or prevent relapses); reducing platelet activation states; alcoholism and alcohol dependence; psychiatric syndromes including anger, rejection sensitivity, and lack of mental of physical energy; late luteal phase dysphoric disorder; premature ejaculation; senile dementia; obesity; Parkinson's disease; or canine affective aggression.

The method can also be employed to inhibit cancer cell growth, in methods for stimulating bone formation by osteoblast stimulation, for treatment of dermatological diseases or disorders such as hyperproliferative or inflammatory skin diseases, and for treatment of premature female orgasm. Each of these embodiments includes the recited methods wherein the subject is identified as in need of the indicated treatment.

More preferably this method is employed to treat one or more diseases or disorders in a subject in need thereof selected from major depressive disorder, obsessive compulsive disorder, panic disorder, social anxiety disorder, generalized anxiety disorder, post-traumatic stress disorder, and premenstrual dysphoric disorder.

In another embodiment, the method is employed to treat menopausal vasomotor symptoms (hot flashes), menopausal vasomotor symptoms with sleep disturbances, menopausal vasomotor symptoms with major depressive disorder, or menopausal vasomotor symptoms with general anxiety disorder in a human in need thereof. In a more specific embodiment, deuterated paroxetine, as described herein, or a pharmaceutically acceptable salt thereof can be dosed as-needed for the treatment of hot flashes, in a subject in need thereof. For example, dosing just prior to bedtime can be utilized to reduce or prevent hot flashes occurring throughout the night, thus alleviating hot flashes and associated sleep disturbances.

In another embodiment, the amount of deuterated paroxetine administered on a daily basis to the human suffering from or susceptible to hot flashes is greater than 20 mg/day and less than about 120 mg/day in an instant release formulation or greater than 25 mg/day and less than about 150 mg/day in a controlled release formulation. In a more specific embodiment, the amount of deuterated paroxetine administered on a daily basis to the human suffering from or susceptible to hot flashes is greater than 60 mg/day and less than about 120 mg/day in an instant release formulation or greater than 75 mg/day and less than about 150 mg/day in a controlled release formulation.

In another embodiment, an effective amount of deuterated paroxetine, as described herein, or a pharmaceutically acceptable salt thereof administered on a daily basis to the human suffering from or susceptible to hot flashes is greater than 5 mg/day and less than about 65 mg/day in an instant release formulation, and more preferably greater than 7.5 mg/day and less than 80 mg/day in a controlled release formulation.

In another embodiment, the method is employed to treat hot flashes in patients who are being treated or have been treated for cancer. In one aspect of this embodiment, the patients are being treated or have been treated for ovarian, breast, or prostate cancer. In a specific embodiment, the subjects are being treated or have been treated with tamoxifen for breast cancer.

Another aspect of the invention is deuterated paroxetine for use in inhibiting the uptake of serotonin in a subject. Preferably that use is in the treatment or prevention in a subject of a disease, disorder or symptom set forth above.

Another aspect of the invention is the use of deuterated paroxetine in the manufacture of a medicament for inhibiting the uptake of serotonin in a subject. Preferably, the medicament is used for treatment or prevention in a subject of a disease, disorder or symptom set forth above.

In another embodiment, the method of treatment further comprises the step of administering to said patient one or more additional therapeutic agents which, alone or in combination with paroxetine, are effective to treat depression, hypertension, generalized anxiety disorder, phobias, post-traumatic stress syndrome, avoidant personality disorder, sexual dysfunction; eating disorders including bulimia, anorexia nervosa, and binge eating; obesity, chemical dependencies, cluster headache, migraine; pain, including neuropathic pain, diabetic nephropathy, post-operative pain, psychogenic pain disorders, and chronic pain syndrome; Alzheimers disease, obsessive-compulsive disorder, panic disorder with or without agoraphobia, memory disorders, Parkinson's diseases, endocrine disorders, vasospasm, cerebellar ataxia, gastrointestinal tract disorders, negative symptoms of schizophrenia, premenstrual syndrome, Fibromyalgia Syndrome; urinary incontinence, including stress incontinence; Tourette's syndrome, trichotillomania, kleptomania, male impotence, cancer, chronic paroxysmal hemicrania and headache in a mammal, sleep-related breathing disorders, cognitive deficits due to aging, stroke, head trauma, neurodegenerative diseases, schizophrenia, anxiety, aggression and stress, disorders of thermoregulation, respiratory disease, bipolar disorder, psychosis, sleep disorder; mania, including acute mania; bladder disorder, genitourinary disorder, cough, emesis, nausea, psychotic disorders such as paranoia and manic-depressive illness, tic disorder, diabetic cardiomyopathy, diabetic retinopathy, cataracts, myocardial infarction, prolonged fatigue, chronic fatigue, chronic fatigue syndrome, premature ejaculation, dysphoria, post partum depression, social phobia, disruptive behavior disorders, impulse control disorders, borderline personality disorder, attention deficit disorders without hyperactivity, Shy-Drager Syndrome, cerebral ischemia, spinal cord trauma, Huntington's Chorea, amyotrophic lateral sclerosis, AIDS-induced dementia, muscular spasms, convulsions, perinatal hypoxia, hypoxia, cardiac arrest, hypoglycemic neuronal damage, ocular damage and retinopathy, brain edema, tardive dyskinesia, cerebral deficits subsequent to cardiac bypass surgery and grafting, affective disorders, mood disorders, agoraphobia without history of panic disorder, and acute stress disorders; and for reducing the side effects of paroxetine, enhancing or potentiating the activity of paroxetine, or for increasing the duration of pharmacological action of paroxetine.

In yet another embodiment, the method of treatment comprises the further step of administering to said patient one or more therapeutic agents which, alone or in combination with paroxetine, are effective to treat one or more of autism, dyskinesia, dysthymic disorder; obesity due to genetic or environmental causes, polycystic ovary disease, craniopharyngioma, Prader-Willi Syndrome, Froehlich's Syndrome, Type II diabetes, growth hormone deficiency, Turner's Syndrome; pro-inflammatory cytokine secretion or production, jet lag, insomnia, hypersomnia, nocturnal enuresis, restless-legs syndrome, vaso-occlusive events, hyperglycemia, hyperinsulinemia, hyperlipidemia, hypertriglyceridemia, diabetes, insulin resistance, impaired glucose metabolism, conditions of impaired glucose tolerance (IGT), conditions of impaired fasting plasma glucose, glomerulosclerosis, syndrome X, coronary heart disease, angina pectoris, vascular restenosis, endothelial dysfunction, impaired vascular compliance, or congestive heart failure; or to increase the onset of action of paroxetine.

Specific second therapeutic agents useful in the method of treatment are the same as those described above as part of combination compositions.

In a more specific embodiment, the combination therapies of this invention include co-administering deuterated paroxetine and: a) clozapine for the treatment of a patient suffering from or susceptible to panic disorder, post-traumatic stress disorder, depression or depressive mood; b) vestipitant for the treatment of a patient suffering from or susceptible to tinnitus or social anxiety disorder; c) quetiapine for the treatment of a patient suffering from or susceptible to general anxiety disorder or post-traumatic stress disorder; or d) naltrexone for the treatment of a patient suffering from or susceptible to alcoholism or alcohol dependence.

Because deuterated paroxetine, as described herein, or a pharmaceutically acceptable salt thereof shows reduced inhibition of cytochrome P450 2D6 (CYP2D6) as compared to paroxetine, the contraindication of co-dosing paroxetine with therapeutic agents that are metabolized by CYP2D6 can be avoided. The replacement of paroxetine with deuterated paroxetine, as described herein, or a pharmaceutically acceptable salt thereof in the treatment of a patient who is also being administered a therapeutic agent that is metabolized by CYP2D6 represents an improvement in a method of treating a patient suffering from of susceptible to both: a condition that is treatable with paroxetine (e.g., one or more disease or disorder described above); and a condition that is treatable by a therapeutic agent that is metabolized by CYP2D6. Therapeutics that are CYP2D6 substrates are known in the art (see http://medicine.iupui.edu/flockhart/2D6.htm#2D6sub), as are the diseases and conditions which they are used to treat.

Thus, in one embodiment, the patient to be administered a compound or composition of this invention has already been administered one or more therapeutic agents that are metabolized CYP2D6, preferably within the 24 hours preceding administration of the compound or composition of this invention. In a specific embodiment, the additional therapeutic agent is selected from nortriptyline, amitriptyline, imipramine, desipramine, fluoxetine, phenothiazines, Type IC antiarrhythmics (e.g., propafenone, flecamide, and encamide), risperidone, thioridazine, tamoxifen, and atomoxetine.

In another embodiment, any of the aforementioned methods comprising the step of administering a compound or composition of this invention to a patient further comprise the additional step of administering to the patient one or more additional therapeutic agents that are metabolized CYP2D6. In a specific embodiment, the additional therapeutic agent is selected from nortriptyline, amitriptyline, imipramine, desipramine, fluoxetine, phenothiazines, Type IC antiarrhythmics (e.g., propafenone, flecamide, and encamide), risperidone, thioridazine, tamoxifen, and atomoxetine.

In each of the above embodiments, the second therapeutic agent or agents may be administered together with deuterated paroxetine, as described herein, as part of a single dosage form or as separate dosage forms. Alternatively, the second therapeutic agent or agents may be administered prior to, consecutively with, or following the administration of deuterated paroxetine, as described herein. In such combination therapy treatment, both the compounds of this invention and the second therapeutic agent(s) are administered by conventional methods. The administration of the second therapeutic agent(s) may occur before, concurrently with, and/or after the administration of deuterated paroxetine. When the administration of the second therapeutic agent occurs concurrently with deuterated paroxetine, as described herein, the two (or more) agents may be administered in a single dosage form (such as a composition of this invention comprising deuterated paroxetine, as described herein, a second therapeutic agent or agents as described above, and a pharmaceutically acceptable carrier), or in separate dosage forms. The administration of a composition of this invention comprising both deuterated paroxetine, as described herein, and a second therapeutic agent(s) to a subject does not preclude the separate administration of said second therapeutic agent(s), any other therapeutic agent or any compound of this invention to said subject at another time during a course of treatment.

Effective amounts of second therapeutic agent or agents useful in the methods of this invention are well known to those skilled in the art and guidance for dosing may be found in patents referenced herein, as well as in Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the optimal effective-amount range of the additional agent(s).

In one embodiment of the invention where one or more second therapeutic agents are administered to an animal, the effective amount of deuterated paroxetine, as described herein, is less than its effective amount would be where the second therapeutic agent(s) are not administered. In another embodiment, the effective amount of the second therapeutic agent is less than its effective amount would be where the deuterated paroxetine is not administered (i.e., the amount of each second therapeutic agent(s) administered in a monotherapy). In this way, undesired side effects associated with high doses of either agent may be minimized. Other potential advantages (including without limitation improved dosing regimens and/or reduced drug cost) will be apparent to those of skill in the art.

According to another aspect, the invention provides deuterated paroxetine and one or more of the above-described second therapeutic agents, either in a single composition or as separate dosage forms for use in the treatment or prevention in a subject of a disease, disorder or symptom set forth above.

In yet another aspect, the invention provides the use of deuterated paroxetine and one or more of the above-described second therapeutic agents in the manufacture of a medicament, either as a single composition or as separate dosage forms, for treatment or prevention in a subject of a disease, disorder or symptom set forth above.

The compounds of this invention may be readily assayed for biological activity by known methods. For instance, in vitro methods of determining binding to the serotonin transporter are available using recombinant cell lines, e.g. see Poss M A et al., U.S. Pat. No. 6,225,324 to Bristol-Myers Squibb; and ex-vivo brain tissue, e.g. see Young J W et al., U.S. Pat. No. 5,648,396 to Sepracor; and Habert E et al., Eur J Pharmacol 1985 118: 107.

Animal models of depression provide reproducible readouts that correlate with human clinical response to antidepressant drugs, including serotonin reuptake inhibitors and specifically paroxetine. For instance, see Porsolt R D et al., Eur J Pharmacol 1979 57: 201; Detke M J et al., Psychopharmacology 1995 121: 66; "Drug Discovery and Evaluation", Vogel H G and Vogel W H (eds.), p. 304, 1997, Springer-Verlag, New York; and El Yacoubi M et al., Proc Natl Acad Sci USA 2003 100: 6227; for descriptions of the well-known forced swim test and tail suspension test. Each of the compounds of this invention may be tested in such animal models.

The rate of metabolism of compounds of this invention may be determined and compared to that of paroxetine in the presence, for instance, of heterologously expressed CYP2D6, or human liver microsomes (both available from BD Gentest, Woburn, Mass.). The compounds may also be tested in whole animals e.g. by oral or parenteral administration, measuring the disappearance of the administered compound and, if desired, the appearance of metabolites. Means for such measurements are well known, e.g. see Segura M et al., Rapid Commun Mass Spectrom, 2003, 17:1455; and Hartter S et al., Ther Drug Monit, 1994, 16:400. The inactivation of CYP2D6 by compounds of this invention may also be measured by known means to determine relevant enzymatic parameters such as $k_{INACT}$. See for instance Bertelsen K M et al., Drug Metab Dispos, 2003, 31:289. The effects of deuterated paroxetine on other drugs known to be metabolized by cytochrome 2D family enzymes may also be measured and compared to the corresponding effects caused by paroxetine; e.g. see Hashimoto K et al., Eur J Pharmacol, 1993, 228:247. This interaction may be measured after either a single dose of paroxetine and deuterated paroxetine, or after repeated doses to measure cumulative cytochrome inactivation.

Diagnostic Methods and Kits

According to another embodiment, the invention provides a method of determining the concentration of paroxetine in a biological sample, said method comprising the steps of:
  a) adding a known concentration of deuterated paroxetine to said biological sample;
  b) subjecting said biological sample to a measuring device that distinguishes paroxetine from deuterated paroxetine;
  c) calibrating said measuring device to correlate the detected quantity of paroxetine with the known concentration of deuterated paroxetine added to said biological sample;
  d) measuring the quantity of paroxetine in the biological sample with the calibrated measuring device; and
  e) determining the concentration of paroxetine in said biological sample by comparing the detected quantity of paroxetine with the detected quantity and known concentration deuterated paroxetine.

Measuring devices that can distinguish paroxetine from said second compound include any measuring device that can distinguish between two compounds that are of identical structure except that one contains one or more heavy atom isotope versus the other. Preferably, such a measuring device is a mass spectrometer, NMR spectrometer, or IR spectrometer.

In another preferred embodiment, the method comprises the additional step of separating both paroxetine and said second compound from said biological sample by organic or solid phase extraction prior to step b).

In another embodiment, the invention provides a method of evaluating the metabolic stability of deuterated paroxetine, comprising the steps of contacting deuterated paroxetine with a metabolizing enzyme source for a period of time; and comparing the amount of said compound and metabolic products of said compounds after said period of time.

In a related embodiment, the invention provides a method of evaluating the metabolic stability of deuterated paroxetine in a patient following administration of deuterated paroxetine. This method comprises the steps of obtaining a serum, urine or feces sample from the patient at a period of time following the administration of the deuterated paroxetine to the subject; and comparing the amount of deuterated paroxetine with the metabolic products of deuterated paroxetine in the serum, urine or feces sample.

The present invention also provides kits for use to treat major depressive disorder, obsessive compulsive disorder, panic disorder, social anxiety disorder, generalized anxiety disorder, post-traumatic stress disorder, premenstrual dysphoric disorder, or menopausal vasomotor symptoms (hot flashes). These kits comprise (a) a pharmaceutical composition comprising deuterated paroxetine or a salt, hydrate, or solvate thereof, wherein said pharmaceutical composition is in a container; and (b) instructions describing a method of using the pharmaceutical composition to treat major depressive disorder, obsessive compulsive disorder, panic disorder, social anxiety disorder, generalized anxiety disorder, post-traumatic stress disorder, premenstrual dysphoric disorder, or menopausal vasomotor symptoms (hot flashes).

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiments, the kits of this invention may comprise in a separate vessel of container a pharmaceutical composition comprising a second therapeutic agent, such as one of those listed above for use for co-administration with a compound of this invention.

EXAMPLES

Example 1

Synthesis of 3,4-Dideuteroxybenzaldehyde (XI)

Compound XI was prepared as outlined in Scheme 4 below. Details of the conversion are set forth below.

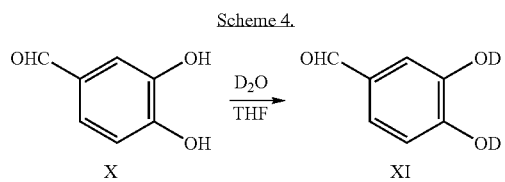

Scheme 4.

Synthesis of 3,4-dideuteroxybenzaldehyde (XI)

To a solution of 3,4-dihydroxybenzaldehyde (X) (40 g) in THF (160 mL) was added $D_2O$ (160 mL) with stirring. The resulting mixture was stirred overnight at room temperature (rt) under nitrogen. The solvent was removed in vacuo and the residue dried in vacuo at 40° C. overnight to provide XI as a solid (40 g). Analysis by 300 MHz $^1$H NMR ($d_6$-DMSO) showed an H/D exchange level of approximately 85%.

Example 2

Alternate Synthesis of 3,4-Dideuteroxybenzaldehyde (XI)

Compound XI was prepared as generally outlined in Scheme 4 above. Details of the conversion are set forth below.

Synthesis of 3,4-dideuteroxybenzaldehyde (XI)

To a solution of 3,4-dihydroxybenzaldehyde (X) (10 g) in acetonitrile (200 mL) was added $D_2O$ (40 mL) and the resulting mixture was stirred for 4 days at rt. The solvent was removed in vacuo to provide XI as a solid. Analysis by 300 MHz $^1$H NMR ($d_6$-DMSO) showed an H/D exchange level of approximately 85%.

Example 3

Alternate Synthesis of 3,4-Dideuteroxybenzaldehyde (XI)

Compound XI was prepared as generally outlined in Scheme 4 above. Details of the conversion are set forth below.

Synthesis of 3,4-dideuteroxybenzaldehyde (XI)

To a solution of 3,4-dihydroxybenzaldehyde (X) (25 g) in $CH_3OD$ (100 mL) was added DCl (0.4 mL) with stirring. The resulting mixture was stirred overnight at rt and the solvent was removed in vacuo. The residue was re-dissolved in $CH_3OD$ (100 mL), DCl (0.4 mL) was added, and the mixture was stirred again overnight at rt. The solvent was removed in vacuo to provide XI as a solid. Analysis by 300 MHz $^1$H NMR ($d_6$-DMSO) showed an H/D exchange level of approximately 85%.

Example 4

Alternate Synthesis of 3,4-Dideuteroxybenzaldehyde (XI)

Compound XI was prepared as generally outlined in Scheme 4 above. Details of the conversion are set forth below.

Synthesis of 3,4-dideuteroxybenzaldehyde (XI)

A 50-L, jacketed reactor equipped with a temperature probe, nitrogenous atmosphere, and reflux condenser was charged with 3,4-dihydroxybenzaldehyde (3.5 kg) and THF (14.0 L). Deuterium oxide (14.0 L) was added and the reaction mixture was stirred for 18 hours (h) at ambient temperature. EtOAc (14 L) was added, and the phases were separated. The aqueous phase was then extracted with EtOAc (14 L). The combined organic layers were concentrated to about 14 L. Toluene was added (14 L) and the suspension was concentrated back down to 14 L. This solvent-swap procedure was repeated two additional times with toluene (14 L each). The solid was collected, and the resulting cake was washed with toluene (10 L). The batch was then dried under high vacuum (40° C.) for 20 h. 3,4-Dideuteroxybenzaldehyde was isolated as a tan solid (3480 g, 98% yield, greater than 99.9% AUC by HPLC, 300 MHz $^1$H NMR indicated a deuteration level of approximately 91%).

Example 5

Synthesis of 2,2-$d_2$-Benzo[d][1,3]-dioxole-5-carbaldehyde (XIV)

Compound XIV was prepared as outlined in Scheme 5 below. Details of the synthesis are set forth below.

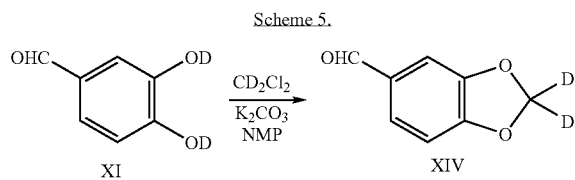

Scheme 5.

Synthesis of 2,2-$d_2$-benzo[d][1,3]dioxole-5-carbaldehyde (XIV)

A suspension of $K_2CO_3$ (29.6 g, 0.22 mol) in N-methylpyrrolidinone (NMP) (270 mL) was heated to 110° C. and stirred under $N_2$. A solution of 3,4-dideuteroxybenzaldehyde (XI) (15 g, 0.11 mol) in $CD_2Cl_2$ (68 mL, 1.1 mol) and NMP (30 mL) was added dropwise over 45 minutes (min). The reaction mixture was stirred at 110° C. for an additional 90 min. The mixture was allowed to cool, was filtered, and the filtrate was poured into water (900 mL) and extracted with EtOAc (3×600 mL). The combined organics were washed with water (2×600 mL), dried (MgSO$_4$), filtered and concentrated in vacuo. The residue was purified by silica-gel chromatography (4:1 Hexane/EtOAc) to give 14.2 g (87%) of XIV as a pale brown oil that solidified on standing. The level of CHD and CH$_2$ present was determined to be approximately 0.5% and approximately 0.03% respectively. (See below).

Quantification of the Amount of the Monodeutero-Product in 2,2-$d_2$-Benzo[d][1,3]dioxole-5-carbaldehyde (XIV)

Due to the very low levels of the CHD present in XIV, routine procedures such as the use of an external standard for comparison of NMR integration values do not allow sufficient accuracy of measurement. The procedure employed here makes use of $^{13}$C—$^1$H coupling of the aldehyde signal (a consistent internal comparison) to measure the amount of the CHD present in a sample of XIV. As the natural abundance of $^{13}$C in carbon is 1.11%, the integration for each signal in the doublet pattern of the aldehyde signal at about 9.75 ppm ($^{13}$C—$^1$H doublet signals at 9.46 ppm and 10.15 ppm) in the $^1$H NMR spectrum equates to about 0.56% each. Comparison of the integration value of one of the doublet peaks versus the CHD signal at 6.03 ppm indicates approximately equal value and therefore the level of CHD in the XIV sample is determined to be about 0.5%. Similarly, the CH$_2$ peak at 6.05 ppm has a level of about 0.03%. 300 MHz $^1$H NMR (XIV) (CDCl$_3$) δ=6.89, 6.92 (d, 1H); 7.30, 7.31, 7.37, 7.38, 7.40, 7.41 (m, 2H); and 9.79 (s, 1H). For the corresponding $d_2$-benzo[d][1,3]dioxole prepared from dihydroxybenzaldehyde (X) the level of the CHD peak was determined to be 6%. The level of the CH$_2$ peak was determined to be at the limit of quantification by 300 MHz $^1$H NMR.

Example 6

Alternate synthesis of 2,2-$d_2$-Benzo[d][1,3]dioxole-5-carbaldehyde (XIV)

Compound XIV was prepared as generally outlined in Scheme 5 above. Details of the synthesis are set forth below.

Synthesis of 2,2-$d_2$-benzo[d][1,3]dioxole-5-carbaldehyde (XIV)

A solution of 3,4-dideuteroxybenzaldehyde (XI) (5 g, 1 eq) in N-methylpyrrolidinone (NMP) (10 mL) and CD$_2$Cl$_2$ (22.3 mL, 10 eq) was added over 1 h to a stirring suspension of K$_2$CO$_3$ (4.9 g, 2 eq) in NMP (100 mL) and D$_2$O (1.5 mL, 2.1 eq) at 110° C. under nitrogen. Stirring was continued at 110° C. for 1.5 h after which time the reaction mixture was cooled to rt, filtered and the solid was washed with ethyl acetate (10 mL). The combined reaction mixture and wash was partitioned between water (50 mL) and ethyl acetate/heptane (4:1, 50 mL). The aqueous layer was separated and extracted with ethyl acetate/heptane (4:1, 3×50 mL). The organic extracts were combined and washed with water (3×60 mL), dried over magnesium sulfate and concentrated in vacuo to a brown oil. The residue was purified by chromatography using ethyl acetate/heptane (1:8) to afford 1.99 g of XIV with a CHD level of 0.59% by 300 MHz $^1$H NMR. The level of the CH2 peak was determined to be at the limit of quantification by 300 MHz $^1$H NMR.

Example 7

Alternate Synthesis of 2,2-$d_2$-Benzo[d][1,3]dioxole-5-carbaldehyde (XIV)

Compound XIV was prepared as generally outlined in Scheme 5 above. Details of the synthesis are set forth below.

Synthesis of 2,2-$d_2$-benzo[d][1,3]dioxole-5-carbaldehyde (XIV)

A 100-L, jacketed reactor equipped with a temperature probe, nitrogenous atmosphere, and reflux condenser was charged with powdered potassium carbonate (4236 g) and NMP (38.7 L). The resulting suspension was heated to 110° C. A pre-mixed solution of 3,4-dideuteroxybenzaldehyde (2150 g), $d_2$-methylene chloride (13.33 Kg) and NMP (4.3 L) was added via an addition funnel. The solution was added over 20 min via subsurface addition. The temperature of the batch had decreased from 110° C. to 100.6° C. over the course of the addition. The batch was allowed to warm back to 110° C., and after 90 min HPLC indicated less than 1% of 3,4-dideuteroxybenzaldehyde. The green-gray suspension was cooled to ambient temperature for 18 h (overnight), and then filtered over a pad of celite. The pad was washed with 4:1 EtOAc/heptane (21.5 L), and the combined filtrates were added to deionized water (54 L). The resulting aqueous mixture was extracted with 4:1 EtOAc/heptane twice (1×32 L, 1×54 L). The combined organic layers were washed with deionized water (3×43 L) and brine (43 L), dried ($MgSO_4$), filtered over celite, and concentrated in vacuo. Crude XIV was isolated as an orange oil which solidified upon standing (2340 g, quantitative yield, 97.6% AUC by HPLC, CHD impurity as determined by 300 MHz $^1$H NMR was 0.41%). The material was further was purified via column chromatography (10.0 kg $SiO_2$ gel, 10 to 20% EtOAc/heptane). The product-containing fractions were concentrated to provide $d_2$-piperonal as light yellow solid (1775 g, 82% yield from 3,4-dideuteroxybenzaldehyde, greater than 99.9% AUC by HPLC, CHD impurity as determined by 300 MHz $^1$H NMR was 0.50%). The level of the $CH_2$ peak was determined to be at the limit of quantification by 300 MHz $^1$H NMR.

Example 8

Synthesis of 2,2-$d_2$-Benzo[d][1,3]dioxol-5-ol (XV)

Compound XV was prepared as outlined in Scheme 6 below. Details of the synthesis are set forth below.

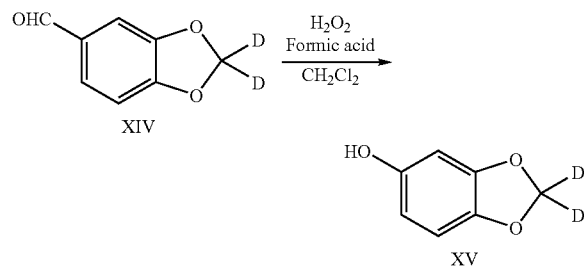

Scheme 6.

Synthesis of 2,2-$d_2$-benzo[d][1,3]dioxol-5-ol (XV)

To a stirred solution of XIV (165 g, 1.08 mol, 1.0 eq) in $CH_2Cl_2$ (5.5 L) was added 30% hydrogen peroxide (343 mL, 3.01 mol, 2.75 eq) and 96% formic acid (182 mL, 4.63 mol, 4.3 eq) and the resulting mixture was stirred overnight at reflux. The reaction mixture was cooled to 0-5° C., 1.5 M NaOH (5.9 L, 8.85 mol, 8.2 eq) was added portionwise over 30 min (exotherm to 25-30° C.) and the mixture was stirred for an additional 30 min. The organic layer was separated and concentrated in vacuo. The residue was dissolved in MeOH (3.6 L), added to the aqueous layer and the resulting mixture stirred at room temperature for 30 min. MeOH was removed in vacuo and the remaining aqueous mixture was extracted with $CH_2Cl_2$ (2 L then 1.5 L), acidified to pH 3 with concentrated aq. HCl then extracted again with $CH_2Cl_2$ (2 L then 2×1.5 L). The combined organics were dried ($MgSO_4$), filtered and concentrated in vacuo. The residue was combined with material from another 165 g batch and purified by column chromatography (hexane/EtOAc 4/1) to give XV (185 g, 61% combined yield) as a white solid with a purity of greater than 95% by 300 MHz $^1$H NMR and 99% by LC. The level of CHD impurity as determined by $^1$H NMR was 1.0%. The level of the $CH_2$ peak was determined to be at the limit of quantification by 300 MHz $^1$H NMR.

Example 9

Alternate Synthesis of 2,2-$d_2$-Benzo[d][1,3]dioxol-5-ol (XV)

Compound XV was prepared as outlined in Scheme 6 above. Details of the synthesis are set forth below.

Synthesis of 2,2-$d_2$-benzo[d][1,3]dioxol-5-ol (XV)

To a 100-L jacketed reactor equipped with a temperature probe, nitrogenous atmosphere, and reflux condenser was added XIV (1990 g) and DCM (20 L). The mixing of these reagents resulted in an endotherm from 20.2° C. to 15.2° C. Formic acid (2720 mL, 4.5 equiv) was added, and the batch was warmed to 25-27° C. Hydrogen peroxide (3874 mL of a 30 wt % solution in water, 2.9 equiv) was then added so as to maintain the internal temperature below 30° C. This addition required 3 h and 15 min. Upon completion of the addition, the batch was stirred for 18 h at 20 to 25° C. HPLC indicated 4.1% XIV remaining. The phases were separated and the organic phase was washed with 25 wt % sodium metabisulfite in water (7.5 L). The organic phase was then cooled to 10-15° C., and an 8.8 wt % solution of sodium hydroxide and water (12 L) was added. This addition was carried out so as to maintain the internal temperature below 20° C. The biphasic mixture was stirred for 30 min at 10-20° C., and then HPLC indicated less than 1% of the intermediate sesamyl formate remaining. The phases were separated, and the aqueous phase was returned to the reactor. MTBE (6 L) was added, followed by 3 N HCl (10 L). The biphasic mixture was stirred for 15 min, and then the phases were separated. The aqueous phase was extracted with MTBE (2×8 L). The combined organic phases were washed with water (8 L) and brine (8 L), dried ($MgSO_4$), filtered over celite, and concentrated to 6 L. Heptane (6 L) was added, and the mixture was concentrated back down to 6 L. This solvent-swap procedure was repeated two additional times with heptane (6 L each time). The resulting off-white suspension was cooled to ambient temperature. The solid was collected, washed with heptane (1 bed volume), and dried under high vacuum. Crude XV was isolated as a yellow solid (1350 g, 74% yield, 97.3% AUC by HPLC, CHD impurity as determined by 300 MHz $^1$H NMR was 0.42%). A portion of the crude material (540 g) was purified via column chromatography (4.4 kg $SiO_2$ gel, 10 to 20% EtOAc/heptane). The product-containing fractions were concentrated to provide XV as an off-white solid (525 g, 69% yield from XIV, greater than 99.9% AUC by HPLC, CHD impurity as determined by $^1$H NMR was 0.55%). The level of the $CH_2$ peak was determined to be at the limit of quantification by 300 MHz $^1$H NMR.

Example 10

Synthesis of (3S,4R)-3-((2,2-$d_2$-Benzo[d][1,3]dioxol-5-yloxy)-methyl-4-(4-fluorophenyl)piperidine Hydrochloride (XVIII)

Compound XVIII was prepared as outlined in Scheme 7 below. Details of the synthesis are set forth below.

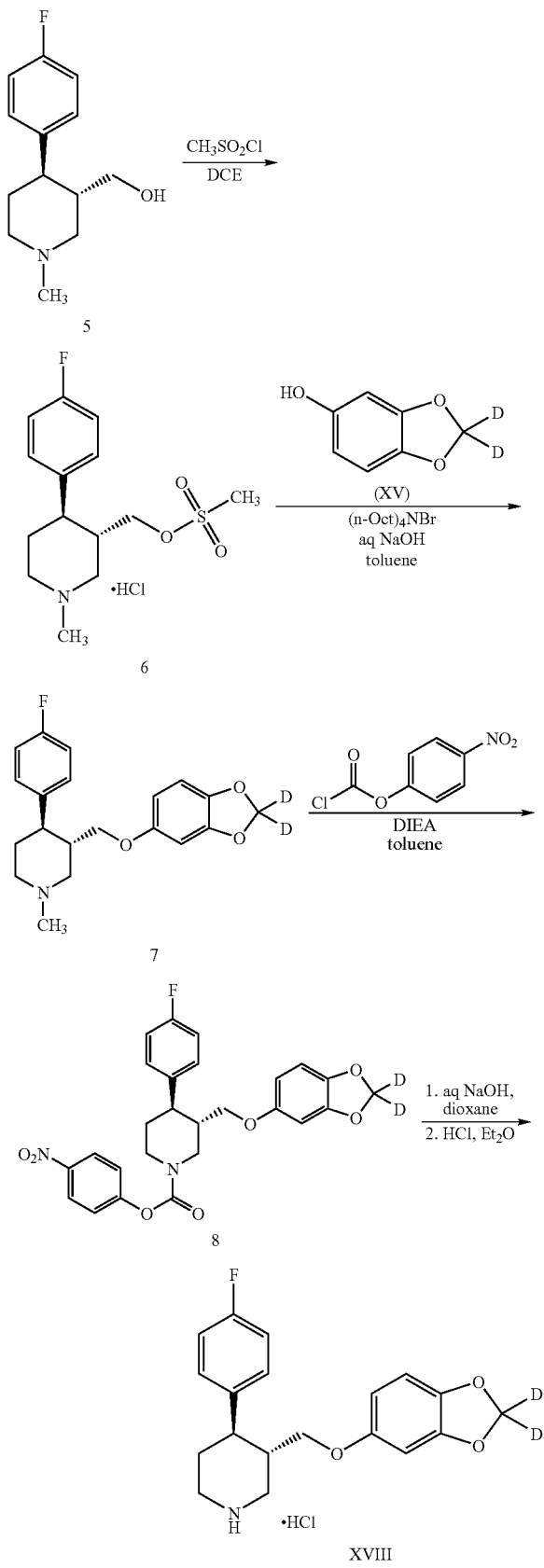

Scheme 7.

Synthesis ((3S,4R)-4-(4-fluorophenyl)-1-methylpiperidin-3-yl)methyl methanesulfonate, HCl salt (6)

((3S,4R)-4-(4-fluorophenyl)-1-methylpiperidin-3-yl) methanol (5) (2.00 g, 8.96 mmol) was dissolved in dichloroethane (20 mL) and methanesulfonyl chloride (0.73 mL) was added. The reaction was stirred for 6 h at rt. The reaction mixture was concentrated on a rotary evaporator to afford 6 as a white solid residue which was suitable for use in crude form. MS m/z: 302.1 (M+H).

Synthesis of (3S,4R)-3-((2,2-$d_2$-benzo[d][1,3]dioxol-5-yloxy)methyl)-4-(4-fluorophenyl)-1-methylpiperidine (7)

To a flask containing crude 6 (approximately 8.96 mmol) was added toluene (45 mL), 2,2-$d_2$-benzo[d][1,3]dioxol-5-ol (XV, 99.7% isotopic purity, 1.26 g, 8.96 mmol), tetra-n-octylammonium bromide (245 mg, 0.448 mmol), and 3M aqueous NaOH (22.4 mL, 67.2 mmol) with stirring. The resulting pale yellow turbid bilayer was stirred and heated in a 90° C. oil bath under a vented air condenser for 5 h. The reaction mixture was cooled to rt and diluted with water (100 mL) and toluene (50 mL). The mixture was poured into a separatory funnel and shaken, and the layers were separated. The organic layer was washed with saturated aqueous NaHCO$_3$ and with brine, then dried over magnesium sulfate, filtered and concentrated on a rotary evaporator to afford approximately 4 g of 7 which contained some residual toluene. This material was suitable for use in crude form. MS m/z: 346.3 (M+H).

Synthesis of (3S,4R)-4-nitrophenyl 3-((2,2-$d_2$-benzo[d][1,3]dioxol-5-yloxy)methyl)-4-(4-fluorophenyl)piperidine-1-carboxylate (8)

To a flask containing crude 7 (approximately 8.96 mmol) was added toluene (60 mL), diisopropylethylamine (0.312 mL, 1.79 mmol) and 4-nitrophenylchloroformate (1.81 g, 8.96 mmol). The mixture was stirred and heated in an 80° C. oil bath under a vented air condenser for 5 h. The reaction mixture was cooled to rt and diluted with toluene (50 mL). The mixture was poured into a separatory funnel and the flask was rinsed with an additional 50 mL of toluene. A 100-mL portion of water was added to the separatory funnel and the layers were shaken and separated. The aqueous layer was extracted with an additional 25 mL of toluene. The combined organic layers were washed with brine, dried over magnesium sulfate, filtered and concentrated on a rotary evaporator to afford an amber oil. The material was purified via column chromatography (5% to 30% EtOAc/hexanes) to provide 2.16 g of 8.

Synthesis of (3S,4R)-3-((2,2-$d_2$-benzo[d][1,3]dioxol-5-yloxy)methyl)-4-(4-fluorophenyl)piperidine, HCl salt (XVIII)

To a solution of 8 (2.16 g, 4.35 mmol) in dioxane (29 mL) was added 2M aqueous NaOH (43.5 mL, 87.0 mmol) and the mixture was stirred and heated in a 70° C. oil bath under a vented air condenser for 3 h. The reaction mixture was cooled to rt and concentrated on a rotary evaporator to remove the majority of the dioxane. The aqueous residue was poured into a separatory funnel and extracted three times with Et$_2$O. The combined organic layers were washed with 1N aqueous NaOH, then dried over magnesium sulfate, filtered and concentrated on a rotary evaporator to afford the free base of XVIII as a pale yellow oil (1.2 g). This material was purified via preparative HPLC/MS to provide 710 mg of the free base of XVIII, which was then taken up in a minimal volume of acetone and added slowly to a stirred solution of 1M HCl/Et$_2$O (5 mL), Et$_2$O (15 mL), and hexanes (60 mL). The resulting cloudy white mixture was held at 0° C. for 1 h, then concentrated to a reduced volume on a rotary evaporator. The resulting white solids were filtered, washed with hexanes/Et$_2$O, and dried in a vacuum oven at 35 to 40° C. overnight to provide 651 mg of the HCl salt of XVIII. $^1$H-NMR (300 MHz, DMSO-d$_6$): δ 9.04 (br s, 2H), 7.25-7.14 (m, 4H), 6.74 (d, 1H, J=8.3), 6.48 (d, 1H, J=2.9), 6.18 (dd, 1H, J=2.4, 8.3), 3.58 (dd, 1H, J=3.4, 10.2), 3.52-3.47 (m, 2H), 3.39-3.35 (m, 1H), 3.01-2.91 (m, 2H), 2.86 (dt, 1H, J=3.4, 12.2), 2.47-2.39 (m, 1H), 2.05-1.94 (m, 1H), 1.88-1.85 (m, 1H). MS (M+H): 332.0.

Example 11

Alternative Synthesis of (3S,4R)-3-((2,2-d$_2$-Benzo[d][1,3]dioxol-5-yloxy)-methyl-4-(4-fluorophenyl)piperidine Hydrochloride (XVIII)

Compound XVIII was prepared as outlined in Scheme 8 below. Details of the synthesis are set forth below.

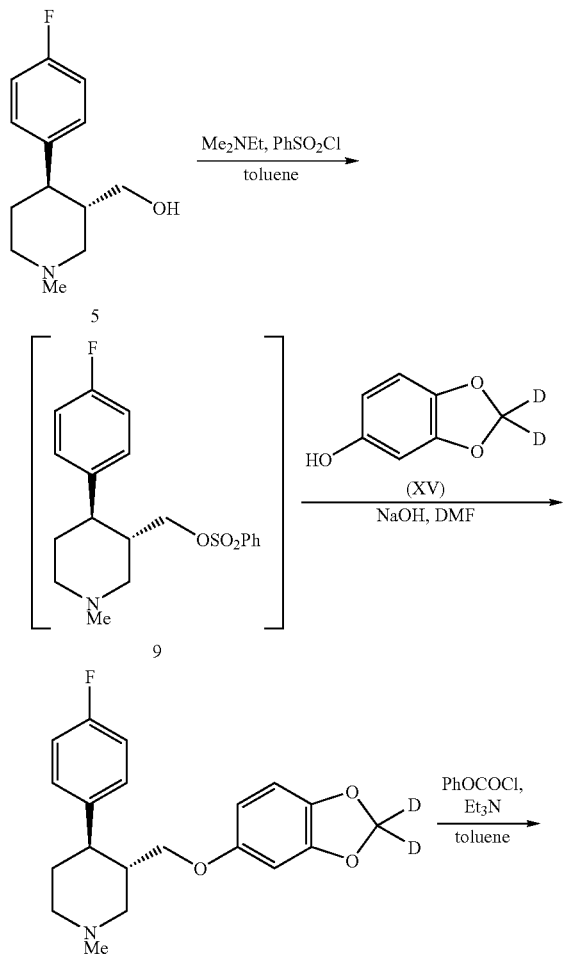

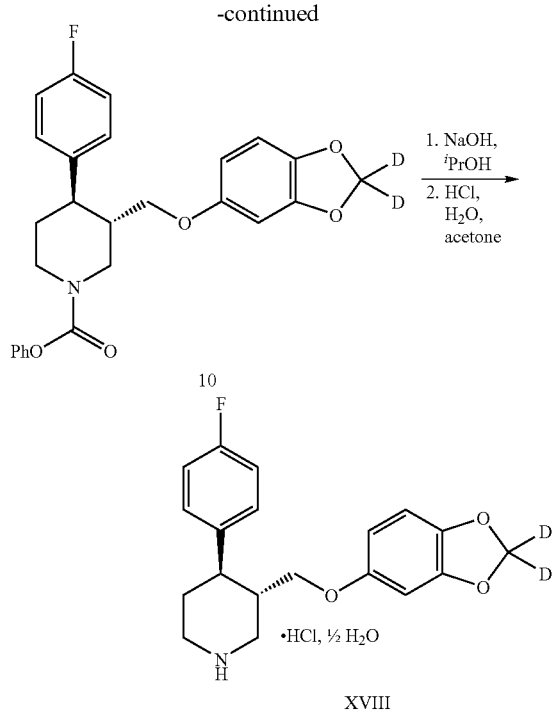

Alternative Synthesis of (3S,4R)-3-((2,2-d$_2$-benzo[d][1,3]dioxol-5-yloxy)methyl)-4-(4-fluorophenyl)-1-methylpiperidine (7)

A solution of 50 g of compound 5 (224 mmol) in toluene (230 mL) was cooled to <5° C. and then 48.8 mL (450 mmol, 2.0 equiv) dimethylethylamine was added. To the reaction mixture was charged a solution of 48.23 g (0.273 mmol, 1.22 eq) benzenesulfonyl chloride in toluene (37.1 mL), keeping the temperature of the reaction mixture at less than or equal to 10° C. The mixture was stirred at 0-5° C. for 110 min. The reaction mixture was then quenched with a solution of 30.5% NaOH (7.5 mL, 37 mmol, 0.34 equiv) and water (140 mL). After stirring for 15 min, the aqueous layer was removed and discarded. The solution of compound 9 was stored at 0° C. overnight. To the organic layer was added 31.4 g of XV (1.0 equiv, 224 mmol), DMF (230 mL) and 10.75 g NaOH (1.2 equiv, 67.2 mmol). The reactor was heated to 71° C. and stirred for 3 h. The reaction mixture was cooled to 50° C. and quenched with water (149 mL). The aqueous layer was extracted with toluene (100 mL) at 50° C. Then the aqueous layer was removed, and the two organic layers were combined. This organic layer was washed with sodium hydroxide solution (prepared by mixing 53 mL of 30.5% sodium hydroxide and 141 mL water) at 50° C. The aqueous layer was removed, and the organic layer was again washed with purified water (149 mL) at 50° C. The organic layer was concentrated at 50-55° C. under vacuum to 2 volumes and then isopropyl alcohol (IPA) (225 mL) was added. The mixture was heated and concentrated at constant volume with introduction of fresh IPA until the refractive index of the distillate was 1.377 (consistent with pure IPA). At this point the mixture was cooled to 45° C., seeded and aged for 90 min. At this point crystallization occurred. The temperature was lowered to 0° C. over 2 h and 30 min and the mixture was held at that temperature for 3 h. The solid was filtered and washed with cold isopropyl alcohol (36 mL). The solid was vacuum dried for 4 h at 40° C. to afford 55.7 g of compound 7 (72% yield).

Synthesis of (3S,4R)-4-phenyl 3-((2,2-d$_2$-benzo[d][1,3]dioxol-5-yloxy)methyl)-4-(4-fluorophenyl)piperidine-1-carboxylate (10)

A solution of 50 g (0.145 mmol) of compound 7 in toluene (365 mL) was heated to 90° C. and then 40.4 g (257 mmol, 1.79 equiv) of phenylchloroformate was charged over approximately 37 minutes. The reaction mixture was heated to 105° C. and stirred for 8 h. The reaction mixture was then cooled to 60° C. and triethylamine (20.9 mL) was added. The reaction mixture was stirred at 60° C. for 1 h, and then cooled to rt. The toluene solution was washed with 10% aqueous sodium hydroxide solution (prepared by mixing 76.5 mL water and 29 mL 30.5% NaOH). The layers were separated and the organic layer was washed with a mixture of water (98.4 mL) and sodium chloride (10 g). After separating the layers, water (105 mL) was added to the toluene solution and the pH was adjusted to <2 using concentrated hydrochloric acid. The aqueous layer was removed and the organic layer was washed three times with 105 mL of water. The organic layer was concentrated at 55-65° C. under vacuum to 2 volumes and then isopropyl alcohol (IPA) (165 mL) was added. The mixture was heated and concentrated to 3 volumes and at this point the refractive index of the distillate was 1.377. IPA (111 mL) was added and the mixture was heated to 70° C. At this temperature the mixture was a pale yellow solution. The mixture was cooled to 64° C., at which temperature crystallization occurred and the mixture was aged for 90 min. Then the mixture was cooled to 0° C. over 150 min and held at that temperature for 120 min. The solids were filtered and washed with cold IPA (35 mL) and then vacuum dried at 40° C. to afford 60.4 g (92%) of compound 10.

Synthesis of (3S,4R)-3-((2,2-d$_2$-benzo[d][1,3]dioxol-5-yloxy)methyl)-4-(4-fluorophenyl)piperidine, HCl salt (XVIII)

A mixture of 40 g (88.6 mmol) of compound 10 and isopropyl alcohol (840 mL) was heated to 79° C. and to the hot reaction mixture was charged a solution of 30.5% sodium hydroxide (131 g, 11.3 equiv) over a period of approximately 45 min. After the addition was completed, the mixture was heated to reflux for 8 h. The reaction mixture was cooled to rt. To the stirring reactor was charged 277 mL water (6.92 vol). This mixture was extracted two times with toluene (123 mL). The toluene extracts were combined and washed three times with 5% aqueous sodium hydroxide solution (114 mL) to remove residual phenol. The toluene solution was then washed with water (123 mL). The organic layer was concentrated to an oil. The oil was dissolved in acetone (229 mL) and this solution was heated to 55° C. and at this point water (7.2 mL) and hydrochloric acid (7.2 mL) were introduced. Then the mixture was cooled to 35° C., seeded, and aged for 2 h. The mixture was further cooled to 20-25° C. in 1 h and n-heptane (95 mL) was added. The mixture was cooled to 0 to 5° C. and held at that temperature for 2 h. The solids were filtered and washed with cold acetone (42 mL). The product was dried under vacuum at 40° C. to give 26.1 g (80%) of the title compound.

Example 12

Investigation of the Drug-Drug Interaction (DDI) Potential Between Deuterated Paroxetine (Test Compound A) and Tamoxifen Tamoxifen's activity against breast cancer is primarily mediated through its 4-hydroxy metabolites, which are formed by the action of cytochrome P450 isozyme CYP2D6. The 4-hydroxy metabolites act as estrogen receptor antagonists in breast tissue. Because tamoxifen conversion to its active metabolites requires CYP2D6, tamoxifen has limited efficacy in phenotypes that are poor CYP2D6 metabolizers and should not be used with other drugs that inactivate the enzyme.

Tamoxifen therapy has been implicated in the occurrence of severe hot flashes. A promising treatment for hot flashes—paroxetine—is also a mechanism-based inactivator of CYP2D6. Since paroxetine-mediated CYP2D6 inactivation would inhibit the formation of the active metabolite endoxifen, its use in breast cancer patients on tamoxifen therapy should be avoided.

Deuterated paroxetine is being developed for the treatment of post-menopausal and tamoxifen-induced hot flashes.

Objective:

The objective of this study was to determine the potential for the deuterated paroxetine, (3S,4R)-3-((2,2-d2-benzo[d][1,3]dioxol-5-yloxy)methyl)-4-(4-fluorophenyl)piperidine, HCl salt-hemihydrate, to inhibit the formation of endoxifen using human cDNA-expressed CYP2D6 as compared with paroxetine. The deuterated paroxetine, (3S,4R)-3-((2,2-d2-benzo[d][1,3]dioxol-5-yloxy)methyl)-4-(4-fluorophenyl)piperidine, HCl salt-hemihydrate, will be referred to as "Test Compound A" in the following examples and the figures.

Tamoxifen (TAM), an antagonist of the estrogen receptor, is metabolized to N-desmethyl TAM by CYP3A4 which in turn is hydroxylated to endoxifen by CYP2D6 (Scheme 9). Endoxifen is an active metabolite with 30-100-fold higher activity than TAM and is the major circulating metabolite in humans.

Scheme 9. Metabolism of N-Desmethyl Tamoxifen to Endoxifen by CYP2D6

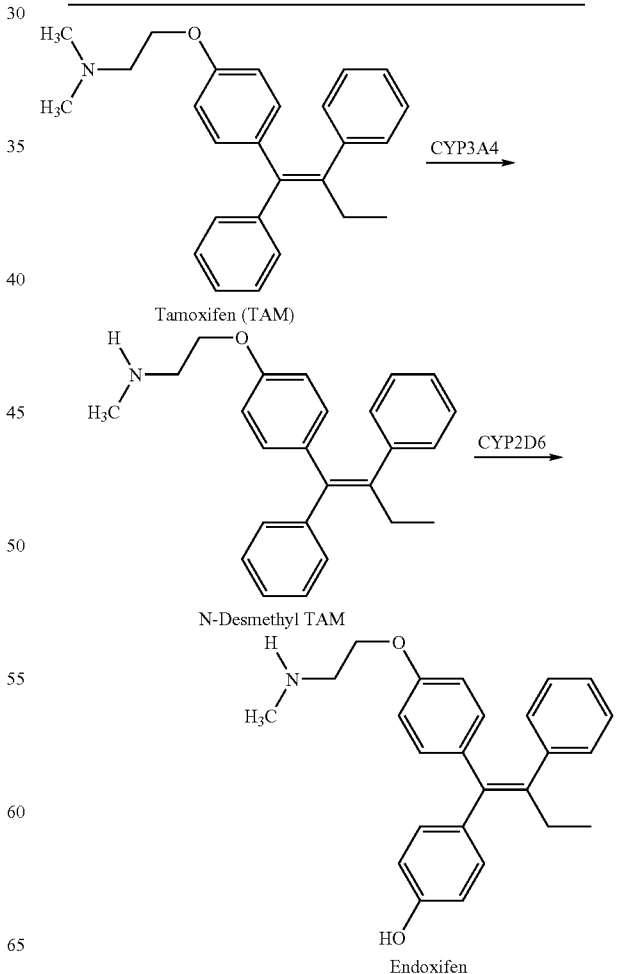

Method:

Test Compound A was pre-incubated for 20 min at various concentrations with human cDNA-expressed CYP2D6 (500 µmol/mL) in the presence of NADPH, after which aliquots of the reaction mixture were diluted 1:10 in buffer containing NADPH. N-desmethyl TAM (50 µM) was then added to the diluted pre-incubation mixtures. After 45 min of incubation, endoxifen concentrations were determined by LC-MS/MS. Similar incubations with paroxetine (reference compound) were performed in parallel.

Results:

There was little to no change in the formation of endoxifen from N-desmethyl tamoxifen over the range of Test Compound A concentrations tested (0-25 µM). Conversely, as concentrations of paroxetine exceeded 5 µM, the rate of endoxifen formation dropped dramatically (FIG. 1). At the highest concentration (25 µM), there was 12-fold more endoxifen produced in the presence of Test Compound A than in the presence of paroxetine. These results confirm that deuterated paroxetine, Test Compound A, is a poor CYP2D6 mechanism-based inactivator and subsequently has a greatly reduced drug-drug interaction potential.

Conclusion:

The maximum plasma concentration of Test Compound A in humans, for vasomotor symptoms (VMS), is not expected to be greater than 30 nM. In this study, Test Compound A had little or no effect on metabolism of N-desmethyl tamoxifen to endoxifen and hence Test Compound A would not be expected to cause clinically relevant drug-drug interactions when co-administered with tamoxifen.

Example 13

Inactivation of CYP2D6 in Human Liver Microsomes by Test Compound A

Objective:

The objective of this study was to evaluate the potential of Test Compound A to inactivate CYP2D6 in human liver microsomes: comparison with paroxetine.

Method:

This study was conducted according to the procedure established by Bertelsen et al for paroxetine. See Bertelsen K M, Venkatakrishnan K, von Moltke L L, Obach S, Greenblatt, D J. Apparent mechanism-based inhibition of human CYP2D6 in vitro by paroxetine: comparison with fluoxetine and quinidine. *Drug Met Disp* 2003; 31:289-293. Briefly, the test articles were pre-incubated with human liver microsomes for various times followed by the addition of dextromethorphan, a CYP2D6 substrate. The formation of dextrorphan, a CYP2D6-specific metabolite of dextromethorphan, was monitored as a measure of CYP2D6 activity.

Figure 2A:
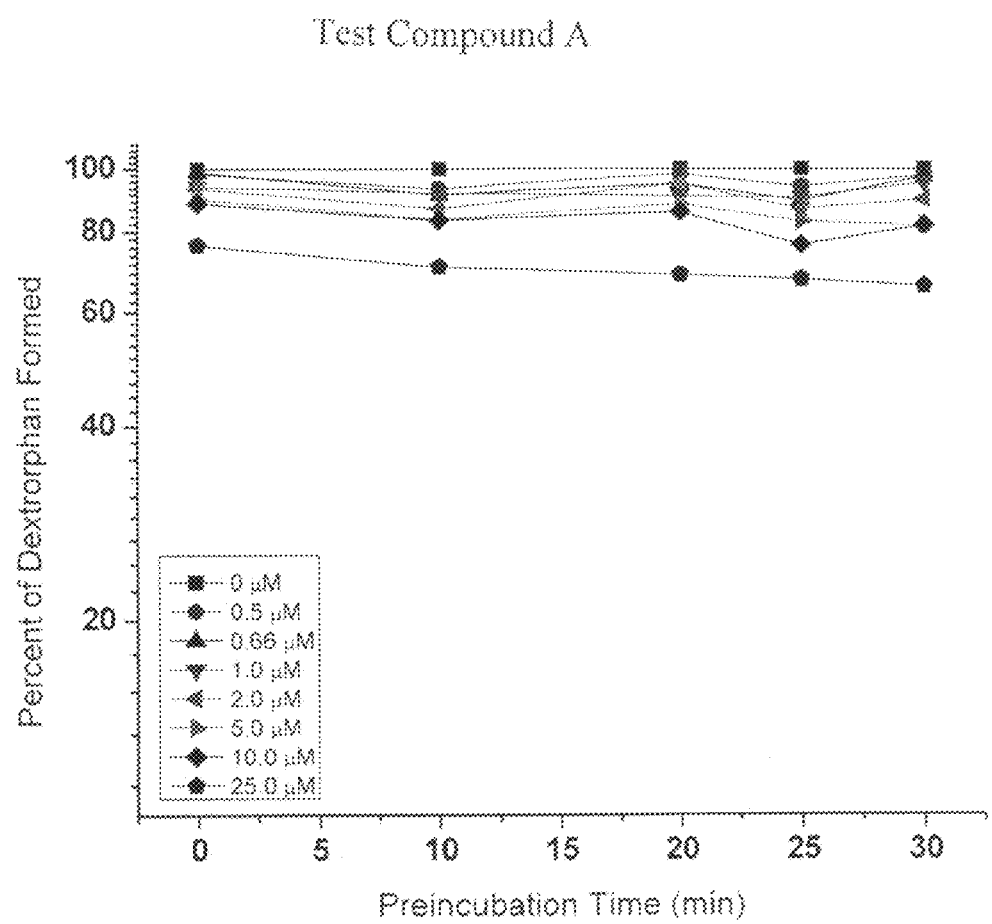
FIGS. 2A and 2B depict the inactivation of CYP2D6 of Test Compound A compared to paroxetine.
Figure 2B:
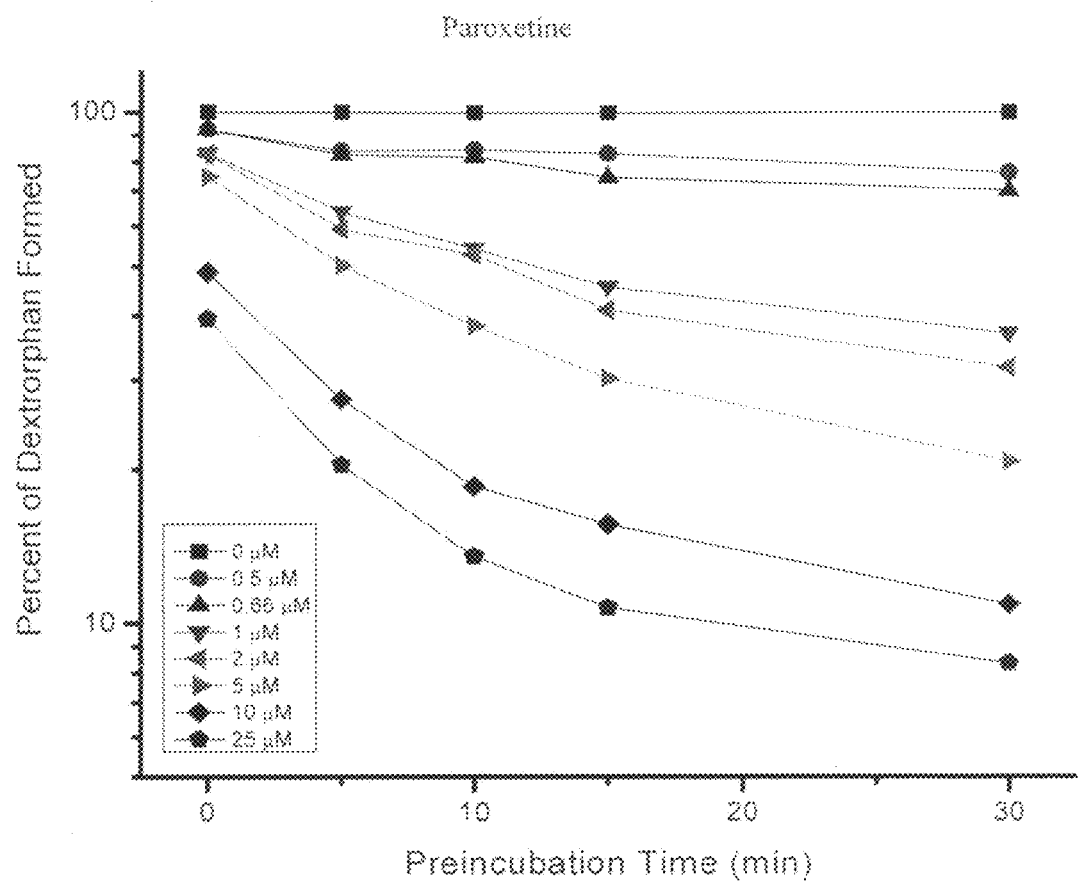
Figure 3:
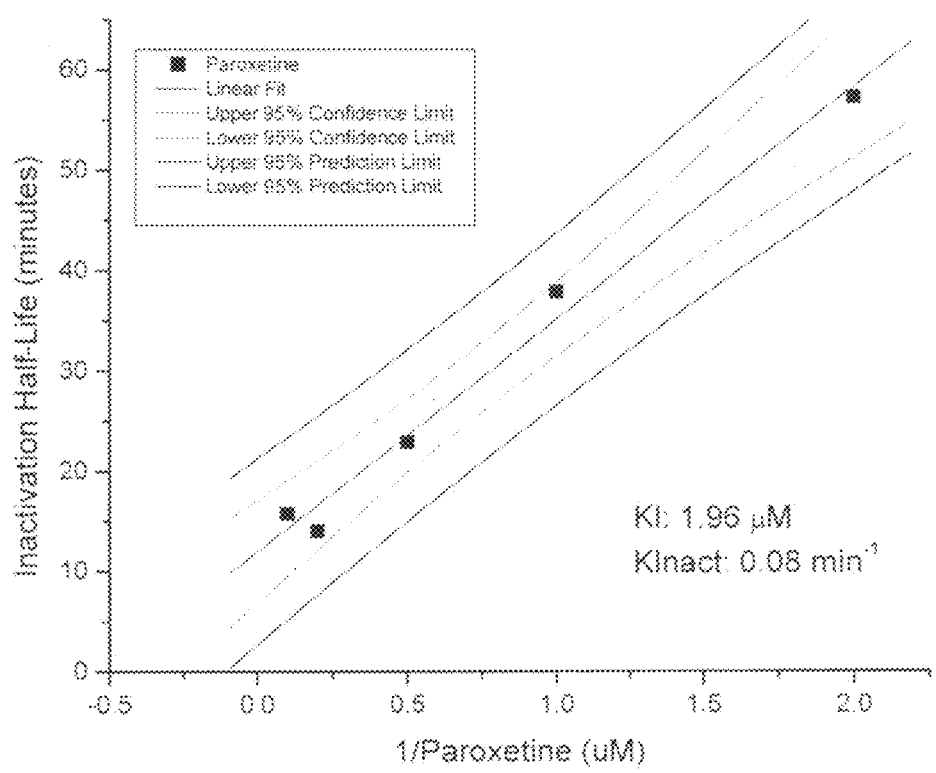
FIG. 3 provides the $k_{INACT}$ curve for paroxetine.

Results:

As previously shown, paroxetine (reference compound) produced a concentration- and time-dependent inhibition of CYP2D6, expressed as the percentage of dextrorphan formation relative to control (FIG. 2). Deuteration appears to significantly diminish this effect, as CYP2D6 activity for Test Compound A remained similar to that of control in the 0-10 µM concentration range. Some inhibition of CYP2D6 occurred as the concentration of Test Compound A approached 25 µM. These results were confirmed by determination of $K_I$ and $k_{INACT}$ for paroxetine-mediated CYP2D6 inactivation (FIG. 3). Paroxetine showed a significant inactivation of CYP2D6 with $K_I$ and $k_{INACT}$ values of 1.96 µM and 0.08 $min^{-1}$ respectively, whereas due to the modest inhibition of CYP2D6, the $k_{INACT}$ of Test Compound A could not be calculated.

Conclusion:

Test Compound A does not exhibit mechanism-based inactivation of CYP2D6 at concentrations up to 10 µM.

Example 14

Metabolic Stability of Deuterated Paroxetine (Test Compound A) in Rat and Human Liver Microsomal Preparations Objective:

The objective of this study was to evaluate the in vitro metabolic clearance of Test Compound A in rat and human liver microsomes: comparison with paroxetine.

Method:

Test Compound A was evaluated at a concentration of 1 µM for apparent metabolic stability by the in vitro $t_{1/2}$ method described by Obach et al. See Obach R S, Baxter J G, Liston T E, Silber B M, Jones B C, MacIntyre F, et al. The prediction of human pharmacokinetic parameters from preclinical and in vitro metabolism data. *JPET* 1997; 283:46-58.

Figure 4:
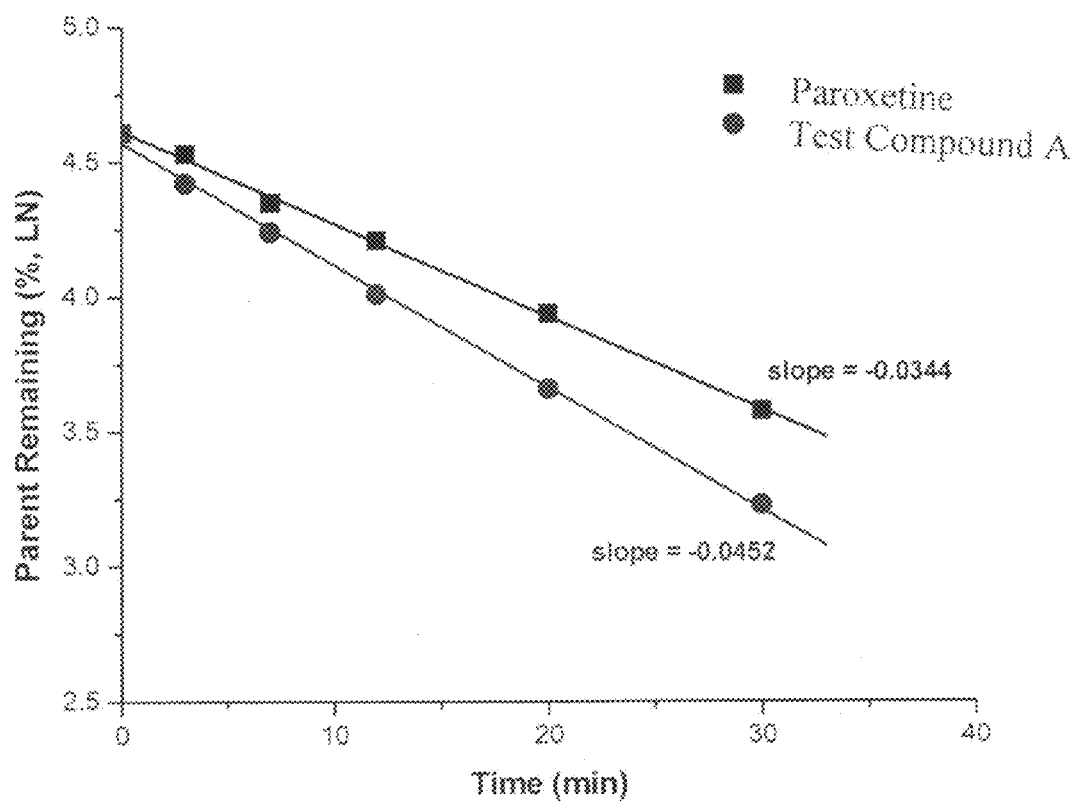
FIG. 4 depicts the metabolic stability of paroxetine and Test Compound A in rat liver microsomes.
Figure 5:
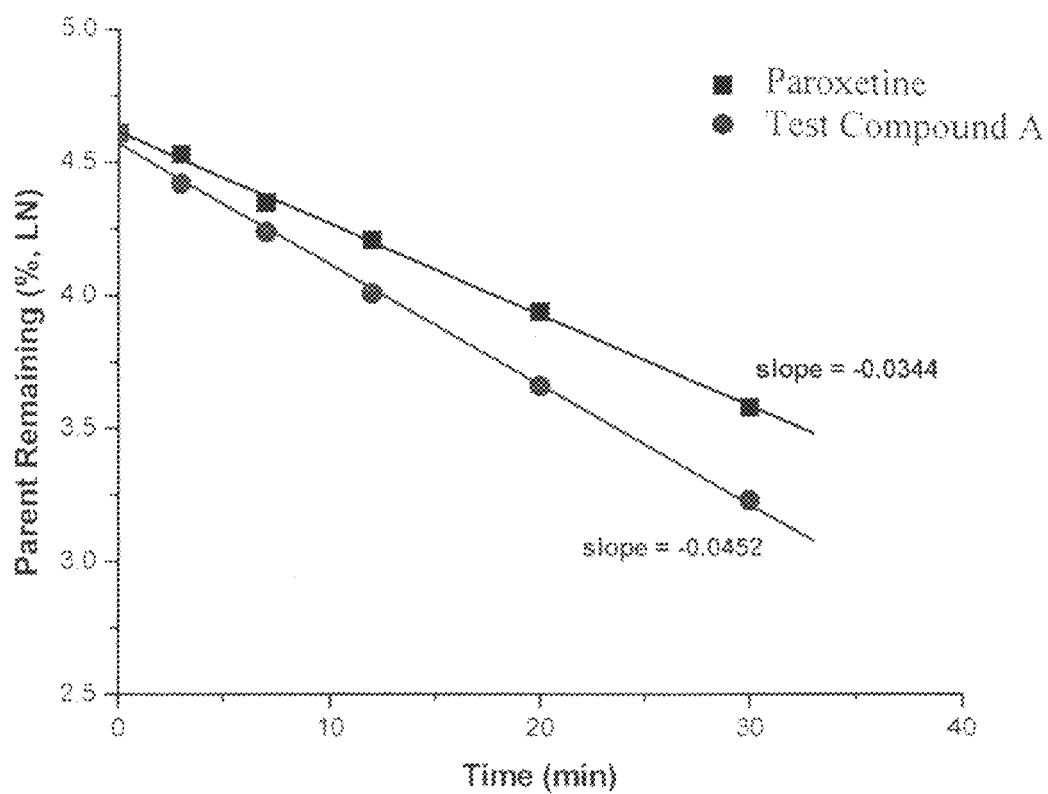
FIG. 5 depicts the metabolic stability of paroxetine and Test Compound A in human liver microsomes.

Results:

Following incubation in rat, and human hepatic microsomes (0.5 mg/mL) the mean relative amounts of Test Compound A remaining at the end of 30 minutes incubation were 25.5±4.3% and 37.2±3.9% (n=4), respectively. The $t_{1/2}$ values, calculated from the LN (% parent remaining) versus time relationship, were 15.5±1.6 and 20.9±2.0 min in rat and human hepatic microsomes, respectively (FIGS. 4 and 5). The metabolic stability of paroxetine was also assessed similarly in parallel and the corresponding $t_{1/2}$ values are shown in Table 1.

TABLE 1

| Species | Test Article | $t_{1/2}$ (min) |
|---------|--------------|-----------------|
| Rat | Test Compound A | 15.5 ± 1.6 |
|  | Paroxetine | 20.4 ± 2.1 |
| Human | Test Compound A | 20.9 ± 2.0 |
|  | Paroxetine | 49.0 ± 7.8 |

Conclusion:

Under the in vitro conditions tested, Test Compound A was readily cleared by metabolic pathways in rat and human liver microsomal preparations. The $t_{1/2}$ values of Test Compound A were approximately 24% and 57% less in rat and human liver microsomes, respectively, than the corresponding values for paroxetine. These data suggest that Test Compound A does not inhibit its own clearance as has been reported for paroxetine. See Bertelsen K M, Venkatakrishnan K, von Moltke L L, Obach S, Greenblatt, D J. Apparent mechanism-based inhibition of human CYP2D6 in vitro by paroxetine: comparison with fluoxetine and quinidine. *Drug Met Disp* 2003; 31:289-293; and Heydom W E. Paroxetine: a review of its pharmacology, pharmacokinetics and utility in the treatment of a variety of psychiatric disorders. *Exp Opin Invest Drugs* 1999; 8(4):417-441. The greater variability observed in the $t_{1/2}$ values of paroxetine in human liver microsomal preparations is likely due the inactivation of its own metabolism.

While this invention has been particularly shown and described with references to preferred embodiments thereof, it will be understood by those skilled in the art that various changes in form and details may be made therein without departing from the scope of the invention encompassed by the appended claims.

What is claimed is:

1. Deuterated paroxetine represented by the following structural formula or a pharmaceutically acceptable salt thereof:

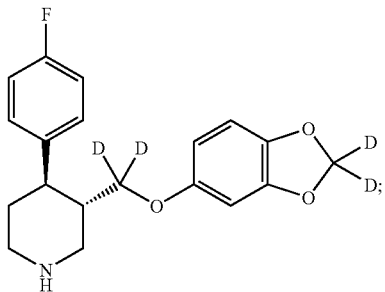

wherein the isotopic enrichment of the benzo[d][1,3]dioxole group with deuterium is at least 99.0%.

2. Deuterated paroxetine represented by the following structural formula or a pharmaceutically acceptable salt thereof:

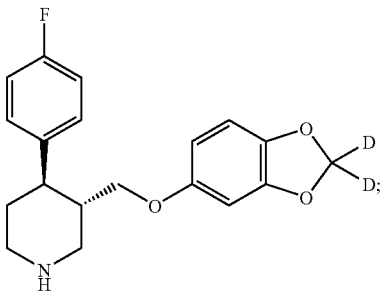

wherein the isotopic enrichment of the benzo[d][1,3]dioxole group with deuterium is at least 99.0%.

3. A pharmaceutical composition comprising the deuterated paroxetine of claim 1 and a pharmaceutically acceptable carrier.

4. A pharmaceutical composition comprising the deuterated paroxetine of claim 2 and a pharmaceutically acceptable carrier.

* * * * *